US 8,399,657 B2

(12) United States Patent
Zhu

(10) Patent No.: US 8,399,657 B2
(45) Date of Patent: Mar. 19, 2013

(54) METHODS FOR INTRODUCING MANNOSE 6-PHOSPHATE AND OTHER OLIGOSACCHARIDES ONTO GLYCOPROTEINS AND ITS APPLICATION THEREOF

(75) Inventor: Yunxiang Zhu, Wayland, MA (US)

(73) Assignee: Genzyme Corporation, Cambridge, MA (US)

( * ) Notice: Subject to any disclaimer, the term of this patent is extended or adjusted under 35 U.S.C. 154(b) by 409 days.

(21) Appl. No.: 12/642,383

(22) Filed: Dec. 18, 2009

(65) Prior Publication Data

US 2010/0173385 A1 Jul. 8, 2010

Related U.S. Application Data

(63) Continuation of application No. 10/943,893, filed on Sep. 20, 2004, now Pat. No. 7,723,296, which is a continuation-in-part of application No. 10/051,711, filed on Jan. 17, 2002, now Pat. No. 7,001,994.

(60) Provisional application No. 60/263,078, filed on Jan. 18, 2001.

(51) Int. Cl.
*A61K 31/715* (2006.01)
*C07H 11/04* (2006.01)
*C07H 1/00* (2006.01)

(52) U.S. Cl. .................. 536/117; 514/54; 536/123.1

(58) Field of Classification Search .................. None
See application file for complete search history.

(56) References Cited

U.S. PATENT DOCUMENTS

| | | | |
|---|---|---|---|
| 4,671,958 A | 6/1987 | Rodwell et al. |
| 4,701,521 A | 10/1987 | Ryser et al. |
| 5,153,312 A | 10/1992 | Porro |
| 5,206,370 A | 4/1993 | Schwartz et al. |
| 5,212,298 A | 5/1993 | Rademacher et al. |
| 5,280,113 A | 1/1994 | Rademacher et al. |
| 5,306,492 A | 4/1994 | Porro |
| 5,324,663 A | 6/1994 | Lowe |
| 5,420,285 A | 5/1995 | Schwartz et al. |
| 5,521,290 A | 5/1996 | Sivam et al. |
| 5,691,154 A | 11/1997 | Callstrom et al. |
| 5,753,520 A | 5/1998 | Schwartz et al. |
| 6,118,045 A | 9/2000 | Reuser et al. |
| 6,156,547 A | 12/2000 | Roth |
| 6,251,858 B1 | 6/2001 | Monsigny et al. |
| 6,399,575 B1 | 6/2002 | Smith et al. |
| 6,472,506 B1 | 10/2002 | Moreau et al. |
| 6,534,300 B1 | 3/2003 | Canfield |
| 6,537,785 B1 | 3/2003 | Canfield |
| 6,569,451 B1 | 5/2003 | Li et al. |
| 6,573,337 B1 | 6/2003 | Toth et al. |
| 6,642,038 B1 | 11/2003 | Canfield |
| 6,670,165 B2 | 12/2003 | Canfield |
| 6,676,963 B1 | 1/2004 | Lanza et al. |
| 6,723,843 B2 | 4/2004 | Toth et al. |
| 6,749,865 B2 | 6/2004 | Calias et al. |
| 6,770,468 B1 | 8/2004 | Canfield |
| 6,800,472 B2 | 10/2004 | Canfield et al. |
| 6,828,135 B2 | 12/2004 | Canfield |
| 6,861,242 B2 | 3/2005 | Canfield |
| 6,905,856 B2 | 6/2005 | Canfield et al. |
| 7,001,994 B2 | 2/2006 | Zhu |
| 7,019,131 B2 | 3/2006 | Wong et al. |
| 7,067,127 B2 | 6/2006 | Canfield |
| 7,160,517 B2 | 1/2007 | Seeberger et al. |
| 7,176,185 B2 | 2/2007 | Hilfinger et al. |
| 7,341,720 B2 | 3/2008 | Stefano |
| 7,723,296 B2 | 5/2010 | Zhu |
| 8,124,073 B2 | 2/2012 | Stefano |
| 2002/0025550 A1 | 2/2002 | Canfield |
| 2002/0137125 A1 | 9/2002 | Zhu |
| 2003/0050299 A1 | 3/2003 | Hirth et al. |
| 2003/0082176 A1 | 5/2003 | LeBowitz et al. |
| 2003/0087868 A1 | 5/2003 | Yew et al. |
| 2003/0119088 A1 | 6/2003 | Canfield et al. |
| 2004/0006008 A1 | 1/2004 | LeBowitz et al. |
| 2004/0132640 A1 | 7/2004 | DeFrees et al. |
| 2005/0003486 A1 | 1/2005 | Canfield et al. |
| 2005/0026823 A1 | 2/2005 | Zankel et al. |
| 2005/0048047 A1 | 3/2005 | Kakkis |
| 2005/0058634 A1 | 3/2005 | Zhu |
| 2005/0169941 A1 | 8/2005 | Lees |
| 2005/0169968 A1 | 8/2005 | Elmaleh et al. |
| 2005/0222244 A1 | 10/2005 | Siegel et al. |
| 2005/0267094 A1 | 12/2005 | Shayman et al. |
| 2005/0281805 A1 | 12/2005 | LeBowitz et al. |
| 2006/0051317 A1 | 3/2006 | Batrakova et al. |
| 2006/0281145 A1 | 12/2006 | Zhu |

(Continued)

FOREIGN PATENT DOCUMENTS

EP 0 384 769 A2 8/1990
WO WO 92/16555 A1 10/1992

(Continued)

OTHER PUBLICATIONS

Tomiya et al., "Calculated Two-Dimenstional Sugar Map of Pyridylaminated Oligosaccharides: Elucidation of the Jack Bean alpha-Mannosidase Digestion Pathway of Man9GlcNac2" Analytical Biochemistry (1991) vol. 193 pp. 90-100.*

(Continued)

*Primary Examiner* — Eric S Olson
(74) *Attorney, Agent, or Firm* — Finnegan, Henderson, Farabow, Garrett & Dunner, L.L.P.

(57) ABSTRACT

Methods to introduce highly phosphorylated mannopyranosyl oligosaccharide derivatives containing mannose-6-phosphate (M6P), or other oligosaccharides bearing other terminal hexoses, to carbonyl groups on oxidized glycans of glycoproteins while retaining their biological activity are described. The methods are useful for modifying glycoproteins, including those produced by recombinant protein expression systems, to increase uptake by cell surface receptor-mediated mechanisms, thus improving their therapeutic efficacy in a variety of applications.

22 Claims, 14 Drawing Sheets

U.S. PATENT DOCUMENTS

| | | | |
|---|---|---|---|
| 2009/0022702 | A1 | 1/2009 | Zhu |
| 2010/0047225 | A1* | 2/2010 | Zhu et al. .................. 424/94.3 |
| 2011/0300120 | A1* | 12/2011 | Avila et al. ................. 424/94.3 |

FOREIGN PATENT DOCUMENTS

| | | | |
|---|---|---|---|
| WO | WO 01/60412 | A2 | 8/2001 |
| WO | WO 01/90139 | A2 | 11/2001 |
| WO | WO 02/07671 | A2 | 1/2002 |
| WO | WO 03/031464 | A2 | 4/2003 |
| WO | WO 03/057179 | A2 | 7/2003 |
| WO | WO 2005/002515 | A2 | 1/2005 |
| WO | WO2005/014035 | * | 2/2005 |
| WO | WO 2005/016973 | A1 | 2/2005 |
| WO | WO 2005/034909 | A2 | 4/2005 |
| WO | WO 2005/077093 | A2 | 8/2005 |
| WO | WO 2005/094874 | A1 | 10/2005 |
| WO | WO 2008/089339 | A2 | 7/2008 |
| WO | WO 2008/089403 | A2 | 7/2008 |

OTHER PUBLICATIONS

Ketcham et al., "Characterization of UDP-N-acetylglucosamine:Glycoprotein N-Acetylglucosamine-1-phosphotransferase from *Acanthamoeba castellanii*" The Journal of Biological Chemistry (1992) vol. 267 No. 16 pp. 11654-11659.*

Takahashi et al., "Oligosaccharide Units of Lysosomal Cathepsin D from Porcine Spleen" The Journal of Biological Chemistry (1983) vol. 258 No. 5, pp. 2819-2830.*

A Guide to IUPAC Nomenclature of Organic Compounds (Recommendations 1993), 1993, Blackwelll Scientific Publications, http://www.acdlabs.com/iupac/nomenclature/, accessed online on Nov. 16, 2009.

Amalfitano et al., *Proc. Natl. Acad. Sci. USA*, 96:8861-8866 (1999). Systemic Correction of the Muscle Disorder Glycogen Storage Disease Type II After Hepatic Targeting of a Modified Adenovirus Vector Encoding Human Acid-α-Glucosidase.

Ashwell et al., *Annu. Rev. Biochem.* 51:531 (1982). Carbohydrate-Specific Receptors of the Liver.

Avigad et al., *J. Biol. Chem.* 237:2736-2743 (1962). The D-Galactose Oxidase of *Polyporus circinatus*.

Baba et al., *Carbohydr. Res.* 177:163-172 (1988). Preparation and Application of a Pentamannosyl Monophosphate-Bovine Serum Albumin Conjugate.

Bandyopadhyay et al., *J. Biol. Chem.* 274:10163-10172 (1999). Nucleotide Exchange in Genomic DNA of Rat Hepatocytes Using RNA/DNA Oligonucleotides.

Bayer et al., *Analyt. Biochem.* 161:123-131 (1987). Enzyme-based detection of glycoproteins on blot transfers using avidin-biotin technology.

Bayer et al., *Anal. Biochem.* 170:271-281 (1988). Biocytin Hydrazide-A Selective Label for Sialic Acids, Galactose, and Other Sugars in Glycoconugates Using Avidin-Biotin Technology.

Bernstein et al., *Carbohydr. Res.* 78:C1-C3 (1980). A general synthesis of model glycoproteins: coupling of alkenyl glycosides to proteins, using reductive ozonolysis followed by reductive amination with sodium cyanoborohydride.

Bijvoet et al., *Hum. Mol. Gen.* 7:53-62 (1998). Generalized Glycogen Storage and Cardiomegaly in a Knockout Mouse Model of Pompe Disease.

Bijvoet et al., *Hum. Mol. Gen.* 8:2145-2153 (1999). Human Acid α-Glucosidase from Rabbit Milk has Therapeutic Effect in Mice with Glycogen Storage Disease Type II.

Braslawsky et al., *Cancer Immunol. Immunother.* 33:367-374 (1991). Adriamycin (hydraone)-Antibody Conjugates Require Internalization and Intracellular Acid Hydrolysis for Antitumor Activity.

Bretthauer et al., *Biochemistry* 12:1251-1256 (1973). Characterization of a Phosphorylated Pentasaccharide Isolated from *Hansenula holstii* NRRL Y-2448 Phospomannan.

Chaudhari et al., *Can. J. Chem.* 50:1987-1991 (1972). Coupling of Amino Acids and Amino Sugars with Cyanuric Chloride (2,4,6-Trichloro-s-triazine).

Chen et al., *Protein Expr. Purif.* 20:228-236 (2000). Purification and Characterization of Human a-Galactosidase A Expressed in Insect Cells Using a Baculovirus Vector.

Chen et al., *Mol. Med. Today* 6:245-251 (2000). Towards a Molecular Therapy for Glycogen Storage Disease Type II (Pompe Disease).

Cole-Strauss et al., *Science* 273:1386-1389 (1996). Correction of the Mutation Responsible for Sickle Cell Anemia by an RNA/DNA Oligonucleotide.

Davis, *Chem. Rev.* 102:579-601 (2002). Synthesis of Glycoproteins.

Distler et al., *J. Biol. Chem.* 266:21687-21692 (1991). The Binding Specificity of High and Low Molecular Weight Phosphomannosyl Receptors from Bovine Testes: Inhibition Studies with Chemically Synthesized 6-*O*-Phosphorylated Oligomannosides.

Fielder et al., *J. Immunol.* 105:265-267(1970). An Immunogenic Polysaccharide-Protein Conjugate.

Fujita et al., *J. Pharmacol. Exp. Ther.* 263:971-978 (1992). Targeted Delivery of Human Recombinant Superoxide Dimutase by Chemical Modification with Mono- and Polysaccharide Derivatives.

Furbish et al., *Biochim. Biophys. Acta.* 673:425-434 (1981). Uptake and Distribution of Placental Glucocerebrosidase in Rat Hepatic Cells and Effects of Sequential Deglycosylation.

Gahmberg et al., *Meth. Enzymol.*, 138:429-442 (1987). Nonmetabolic Radiolabeling and Tagging of Glycoconjugates.

Gahmberg et al., *APMIS Suppl.* 27:39-52 (1992). Cell surface carbohydrate in cell adhesion. Sperm cells and leukocytes bind to their target cells through specific oligosaccharide ligands.

Ghose et al., *Meth. Enzymol.* 93:280-333 (1983). Preparation of antibody-linked cytotoxic agents.

Gray, *Arch. Biochem. Biophys.* 163:426-428 (1974). The Direct Coupling of Oligosaccharides to Proteins and Derivatized Gels.

Himmelspach et al., *Eur. J. Immunol.* 163:106-112 (1971). Use of 1-(m-aminophenyl)flavazoles for the preparation of immunogens with oligosaccharide determinant groups.

Hoefsloot et al., *EMBO J.* 7:1697-1704 (1988). Primary structure and processing of lysosomal alpha-glucosidase; homology with the intestinal sucrase-isomaltase complex.

Ioannou et al., *J. Cell Biol.* 119:1137-1150 (1992). Overexpression of Human α-Galacosidase A Results in its Intracellular Aggregation, Crystallization in Lysosomes, and Selective Secretion.

Kakkis et al., *Protein Express. Purif.* 5:225-232 (1994). Overexpression of the Human Lysosomal Enzyme α-L-Iduronidase in Chinese Hamster Ovary Cells.

King et al., *Biochemistry* 25:5774-5779 (1986). Preparation of Protein Conjugates via Intermolecular Hydrazone Linkage.

Kmiec, *Adv. Drug Deliv. Rev.* 17:333-340 (1995). Genetic Manipulation in Mammalian Cells Using an RNA/DNA Chimeric Oligonucleotide.

Kornfeld et al., *Annu. Rev. Cell Biol.*, 5:483-525 (1989). The Biogenesis of Lysosomes.

Kralovec et al., *Cancer Immunol. Immunother.* 29:293-302 (1989). Synthesis of Site-Specific Methotrexate-IgG Conjugates: Comparison of Stability and Antitumor Activity with Active-Ester-Based Conjugates.

Kren et al., *Proc. Natl. Acad. Sci. USA* 96:10349-10354 (1999). Correction of the UDP-Glucuronosyltransferase Gene Defect in the Gunn Rat Model of Crigler-Najjar Syndrome Type I with a Chimeric Oligonucleotide.

Kren et al., *Nature* 4:285-290 (1998). In Vivo Site-Directed Mutagenesis of the *Factor IX* Gene by Chimeric RNA/DNA Oligonucleotides.

Lee et al., *Biochemistry* 15:3956-3963 (1976). 2-Imino-2-Methoxyethyl 1-Thioglycosides: New Reagents for Attaching Sugars to Proteins.

Lemieux et al., *J. Am. Chem. Soc* 97:4076-4083 (1975). The Properties of a Synthetic Antigen Related to the Human Blood-Group Lewis a.

Li et al., *Glycobiology* 1:511-517 (1991). Isolation and Characterization of Mannose 6-Phosphate/Insulin-Like Growth Factor II Receptor from Bovine Serum.

Martiniuk et al., *Proc. Natl. Acad. Sci. USA* 83:9641-9644 (1986).

Matsuura et al., *Glycobiology* 8:329-339 (1998). Human α-Galactosidase A:Characterization of the *N*-Linked Oligosaccharides on the Intracellular and Secreted Glycoforms Overexpressed by Chinese Hamster Ovary Cells.

McBroom et al., *Meth. Enzymol.* XXVII:212-222 (1972). Carbohydrate Antigens: Coupling of Carbohydrates to Proteins by Diazonium and Phenylisothiocyanate Reactions.

McVie-Wylie et al., *Molecular Genetics and Metabolism* 94:448-455 (2008). Biochemical and pharmacological characterization of different recombinant acid -glucosidase preparations evaluated for the treatment of Pompe disease.

Moczar et al., *FEBS Lett.* 50:300-302 (1975). Preparation of N-Acetylglucosamine Derivatives of Proteins.

Molema et al., *J. Med. Chem.*, 34:1137-1141 (1991). Neoglycoproteins as Carriers for Antiviral Drugs: Synthesis of Analysis of Protein-Drug Conjugates.

Montalvo et al., *Mol. Genet. Metab.* 81:203-208 (2004). Glycogenesis type II: identification and expression of three novel mutations in the acid $a$-glucosidase gene causing the infantile form of the disease.

Moreland et al., *J. Biol. Chem.* 280:6780-6791 (2005). Lysosomal Acid $a$-Glucosidase Consists of Four Different Peptides Processed from a Single Chain Precursor.

Mutsaers et al., *Biochimica et Biophysica Acta* 911:244-251 (1987). Determination of the Structure of the Carbohydrate Chains of Acid $a$-Glucosidase From Human Placenta.

O'Shannessy et al., *J. Appl. Biochem.* 7:347-355 (1985). Specific Conjugation Reactions of the Oligosaccharides Moieties of Immunoglobulins.

O'Shannessy et al., *Immunol. Lett.* 8:273-277 (1984). A Novel Procedure for Labeling Immunoglobulins by Conjugation to Oligosaccharide Moieties.

Parolis et al., *Carbohydr. Res.* 309:77-87 (1998). The Extracellular Polysaccharide of *Pichia* (*Hansenula*) *holstii* NRRL Y-2448: The Phosphorylated Side Chains.

Raben et al., *Mol. Gen. Metabol.* 80:159-169 (2003). Enzyme Replacement Therapy in the Mouse Model of Pompe Disease.

Raben et al., *Mol. Ther.*, 6:601-608 (2002). Glycogen Stored in Skeletal but Not in Cardiac Muscle in Acid α-Glucosidase Mutant (Pompe) Mice is Highly Resistant to Transgene-Encoded Human Enzyme.

Raben et al., *Mol. Ther.* 11:48-56 (2005). Replacing Acid $a$-Glucosidase in Pompe Disease: Recombinant and Transgenic Enzymes are Equipotent, but Neither Completely Clears Glycogen from Type II Muscle Fibers.

Raben et al., *J. Biol. Chem.*, 273:19086-19092 (1998). Targeted Disruption of the Acid α-Glucosidase Gene in Mice Causes an Illness with Critical Features of Both Infantile and Adult Human Glycogen Storage Disease Type II.

Rando et al., *Proc. Natl. Acad. Sci. USA*, 97:5363-5368 (2000). Rescue of Dystrophin Expression in *mdx* Mouse Muscle by RNA/DNA Oligonucleotides.

Reuser et al., *Exp. Cell Res.* 155:178-189 (1984). Uptake and Stability of Human and Bovine Acid a-Glucosidase in Cultured Fibroblasts and Skeletal Muscle Cells from Glycogenosis Type II Patients.

Rodriguez et al., *J.Org. Chem.* 63:7134-7135 (1998). Aminooxy-, Hydrazide-, and Thiosemicarbazide-Functionalized Saccharides: Versatile Reagents for Glycoconjugate Synthesis.

Schwartz et al., *Bioconj. Chem.* 2:333-336 (1991). Preparation of Hydrazino-Modified Proteins and Their Use for the Synthesis of $^{99m}$Tc-Protein Conjugates.

Scriver et al., *The Metabolic and Molecular Bases of Inherited Disease*. 8$^{th}$ edition, New York, 2001.

Sears et al., *Science* 291:2344-2350 (2001). Toward Automated Synthesis of Oligosaccharides and Glycoproteins.

Slodki et al., *Biochim. Biophys. Acta* 57:525-533 (1962). Phosphate Linkages in Phospomannans from Yeast.

Srivastava et al., *Carbohydr. Res.*, 161:324-329 (1987). Synthesis of 6'-O-Phosphorylated O-α-D-Mannopyranosyl-(1→6)- α-D-Mannopyranosides.

Srivastava et al., *J. Org. Chem.* 52:2869-2875 (1987). Synthesis of Phosphorylated Pentasaccharides Found on Asparagine-Linked Carbohydrate Chains of Lysosomal Enzymes.

Srivastava et al., *Carbohydr. Res.* 161:195-210 (1987). Synthesis of Phosphorylated Trimannosides Corresponding to End Groups of the High-Mannose Chains of Lysosomal Enzymes.

Srivastava et al., *Carbohydr. Res.* 155:57-72 (1986). Synthesis of the 6- and 6-' Phosphates of 8-Methoxycarbonyloctyl 2-O-α-D-Mannopyranosyl- α-D-Mannopyranoside.

Taylor et al., *Am. J. Physiol. Endocrinol. Metab.* 252:E690-E698 (1987). Uptake and Processing of Glycoproteins by Rat Hepatic Mannose Receptor.

Tolvanen et al., *J. Biol. Chem.* 261:9546-9551 (1986). In Vitro Attachment of Mono-and Oligosaccharides to Surface Glycoconjugates of Intact Cells.

Tomoda et al., *Carbohydr. Res.*, 213:37-46 (1991). Binding Specificity of D-Mannose 6-Phosphate Receptor of Rabbit Alveolar Macrophages.

Tong et al., *J. Biol. Chem.* 264:7962-7969 (1989). Ligand Interactions of the Cation-Independent Mannose 6-Phosphate Receptor.

Townsend et al., *Glycobiol.*, 1:139-147 (1991). Analysis of Glycoprotein Oligosaccharides Using High-pH Anion Exchange Chromatography.

Valenzano et al., *J. Biol. Chem.* 270:16441-16448 (1995). Soluble Insulin-Like Growth Factor II/Mannose 6-Phosphate Receptor Carries Multiple High Molecular Weight Forms of Insulin-Like Growth Factor II in Fetal Bovine Serum.

Van Der Ploeg et al., *J. Clin. Invest.* 87:513-518 (1991). Intravenous Administration of Phosphorylated Acid α-Glucosidase Leads to Uptake of Enzyme in Heart and Skeletal Muscle of Mice.

Van Hove et al., *Proc. Natl., Acad. Sci. USA* 93:65-70 (1996). High-Level Production of Recombinant Human Lysosomal Acid α-Glucosidase in Chinese Hamster Ovary Cells Which Targets to Heart Muscle and Corrects Glycogen Accumulation in Firboblasts from Patients with Pompe Disease.

Varki et al., *J. Biol. Chem.*, 255:10847-10858 (1980). Structural Studies of Phosphorylated High Mannose-Type Type Oligosaccharides.

Vilaseca et al., *Bioconj. Chem.* 4:515-520 (1993). Protein Conjugates of Defined Structure: Synthesis and Use of a New Carrier Molecule.

Wilchek et al., *Meth. Enzymol.* 138:429-442 (1987). Labeling Glycoconjugates with Hydrazide Reagents.

Wu et al., *Front. Biosci.* 7:717-725 (2002). Targeting Hepatocytes for Drug and Gene Delivery: Emerging Novel Approaches and Applications.

Yoon et al., *Proc. Natl. Acad. Sci. USA* 93:2071-2076 (1996). Targeted Gene Correction of Episomal DNA in Mammalian Cells Mediated by a Chimeric RNA-DNA Oligonucleotide.

Zhang et al., *Tetrahedron* 54:11783-11792 (1998). Linking Carbohydrates to Proteins Using N-(2,2-Dimethoxyethyl)-6-hydroxy Hexanamide.

Zhao et al., *Protein Express. Purif.* 19:202-211 (2000). Purification and Characterization of Recombinant Human α-N-Acetylglucosaminidase Secreted by Chinese Hamster Ovary Cells.

Zhou et al., *Anal. Biochem.* 306:163-170 (2002). Mannose 6-Phosphate Quantitation in Glycoproteins Using High-pH Anion-Exchange Chromatography with Pulsed Amperometric Detection.

Zhu et al., *Biochem. J.*, Immediate Publication (2005). Carbohydrate-remodeled acid $a$-glucosidase with higher affinity for the cation-independent mannose 6-phosphate receptor demonstrates improved delivery to muscles of Pompe mice.

Zhu et al., *JBC Papers in Press*, published Sep. 21, 2004 as Manuscript M409676200. Conjugation of Mannose 6-Phosphate-Containing Oligosaccharides to Acid α-Glucosidase Improves the Clearance of Glycogen in Pompe Mice.

Zhu et al., U.S. Appl. No. 10/051,711: Office Action dated Sep. 30, 2003.

Zhu et al., U.S. Appl. No. 10/051,711: Office Action dated Apr. 16, 2004.

Zhu et al., U.S. Appl. No. 10/051,711: Office Action dated Jan. 12, 2005.

Zhu et al., U.S. Appl. No. 10/943,893: Office Action dated Feb. 28, 2007.

Zhu et al., U.S. Appl. No. 10/943,893: Office Action dated Sep. 20, 2007.

Zhu et al., U.S. Appl. No. 10/943,893: Office Action dated Jan. 30, 2008.
Zhu et al., U.S. Appl. No. 10/943,893: Office Action dated Sep. 25, 2008.
Zhu et al., U.S. Appl. No. 10/943,893: Office Action dated Dec. 17, 2008.
Zhu et al., U.S. Appl. No. 11/264,255: Office Action dated Oct. 12, 2007.
Zhu et al., U.S. Appl. No. 11/264,255: Office Action dated Jun. 25, 2008.
Zhu et al., U.S. Appl. No. 12/237,113: Office Action dated Nov. 19, 2009.
Abraham et al., "Heparin-Binding EGF-Like Growth Factor: Characterization of Rat and Mouse cDNA Clones, Protein Domain Conservation Across Species, and Transcript Expression in Tissues" *Biochem. Biophys. Res. Commun.* 190(1):125-133 (1993).
Arakatsu et al., "Immunochemical Studies on Dextrans. V. Specificity and Cross-Reactivity with Dextrans of the Antibodies Formed in Rabbits to Isomaltonic and Isomaltotrionic Acids Coupled to Bovine Serum Albumin" *J. Immunol.* 97(6):858-866 (1966).
Balaji et al., "Molecular dynamics simulation sof high-mannose oligosaccharides" *Glycobiology* 4(4):497-515 (Aug. 1994).
Beesley et al., "Mutational analysis of 85 mucopolysaccharidosis type I families: frequency of known mutations, identification of 17 novel mutations and in vitro expression of missense mutations" *Hum. Genet.* 109(5):503-511 (Nov. 2001; epub Oct. 19, 2001).
Berge et al., "Pharmaceutical Salts" *J. Pham. Sci.* 66:1-19 (1977).
Bond et al., "Structure of a human lysosomal sulfatase" *Structure* 5:277-289 (Feb. 1997).
Branden et al., *Introduction to Protein Structure.* 2d ed. Garland Publishing, Inc., New York: 1999; pp. 358-366.
Brooks et al., "Glycosidase active site mutations in human α-L-iduronidase" *Glycobiology* 11(9):741-750 (2001).
Brooks et al., "A specific fluorogenic assay for N-acetylgalactosamine-4-sulphatase activity using imnunoadsorption" *J. Inher. Metab. Dis.* 14:5-12 (1991).
Caliceti et al., "Pharmacokinetic and Biodistribution Properties of Poly(ethylene glycol)-Protein Conjugates" *Advanced Drug Delivery Reviews* 56:1261-1277 (2003).
Casares et al., "Antigen-specific downregulation of T cells by doxorubicin delivered through a recombinant MHC II-peptide chimera" *Nat. Biotechnol.* 19:142-147 (2001).
Cavallaro et al. "Glycosilated Macromolecular Conjugates of Antiviral Drugs with a Polyaspartamide" *J. Drug Targeting* 12(9-10):593-605 (2004).
Civallero et al., "Twelve different enzyme assays on dried blood filter paper samples for detection of patients with selected inherited lysosomal storage diseases" *Clin. Chim. Acta* 372:98-102 (2006).
Crich et al., "Direct Chemical Synthesis of β-Mannopyranosides and Other Glycosides via Glycosyl Triflates" *Tetrahedron* 54:8321-8348 (1998).
Davis et al., "Glycoprotein Synthesis: From Glycobiological Tools to Tailor-made Catalysts" *Synlett* 9:1495-1507 (1999).
Davis, "Recent Developments in Glycoconjugates" *J. Chem. Soc., Perkin Trans. 1.* 1:3215-3237 (1999).
Day et al., "Induction of Antigen-Specific CTL Responses Using Antigens Conjugated to Short Peptide Vectors" *J. Immunol.* 170:1498-1503 (2003).
Demeule et al., "High transcytosis of melanotransferrin (P97) across the blood-brain barrier" *J. Neurochem.* 83:924-933 (2002).
Deonarain, "Ligand-targeted receptor-mediated vectors for gene delivery" *Exp. Opin. Ther. Patents* 8(1):53-69 (1998).
Derossi et al., "Trojan peptides: the penetratin system for intracellular delivery" *Trends Cell Biol.* 8:84-87 (1998).
Di Francesco et al., "In vitro correction of iduronate-2-sulfatase deficiency by adenovirus-mediated gene transfer" *Gene Ther.* 4(5):442-448 (1997).
Downing et al., "Synthesis of enzymatically active human α-L-iduronidase in *Arabidopsis* cgl (Complex glycandeficient) seeds" *Plant Biotechnol.* 4(2):169-181 (2006).
Düffels et al., "Synthesis of high-mannose type neoglycolipids: active targeting of liposomes to macrophages in gene therapy" *Chem. Eur. J.* 6(8):1416-1430 (2000).

Duncan et al., "A New Reagent Which May Be Used to Introduce Sulfhydryl Groups Into Proteins, and Its Use in the Preparation of Conjugates for Immunoassay" *Anal. Biochem.* 135:68-73 (1983).
Durand et al., "Active-site motifs of lysosomal acid hydrolases: invariant features of clan GH-A glycosyl hydrolases deduced from hydrophobic cluster analysis" *Glycobiology* 7(2):277-284 (1997).
Dvir et al., "X-ray structure of human acid-β-glucosidase, the defective enzyme in Gaucher disease" *EMBO Reports* 4(7):1-6 (2003).
Elliott et al., "Intercellular Trafficking and Protein Delivery by a Herpesvirus Structural Protein" *Cell* 88:223-233 (1997).
Etrych et al., "New HPMA copolymers containing doxorubicin bound via pH-sensitive linkage: synthesis and preliminary in vitro and in vivo biological properties" *J. Controlled Release* 73:89-102 (2001).
European Patent Application No. 06740572.0: Summons to Attend Oral Proceedings at the European Patent Office, dated Mar. 30, 2011.
Fawell et al., "Tat mediated delivery of heterologous proteins into cells" *Proc. Natl. Acad. Sci. U.S.A.* 91:664-668 (Jan. 1994).
Flomen et al., "Determination of the organisation of coding sequences within the iduronate sulphate sulphatase (IDS) gene" *Hum. Mol. Genet.* 2:5-10 (1993).
Gahmberg et al. "Nonmetabolic Radiolabeling and Tagging of Glycoconiugates" *Meth. Enzymol.* 230:32-45 (1994).
Garman et al., "Structural Basis of Fabry Disease" *Mol. Genet. Metabol.* 77(1-2):3-11 (2002).
Garman et al., "The Molecular Defect Leading to Fabry Disease: Structure of Human α-Galactosidase" *J. Mol. Biol.* 337:319-335 (2004).
GenBank Accession No. AI587087, "tr53a08.xl NCI_CGAP_Pan1 *Homo sapiens* cDNA clone Image:2222006 3- similar to gb:X59960 Sphingomyelin Phosphodiesterase Precursor (Human);, mRNA sequence" (1997).
GenBank Accession No. NM_000152, "*Homo sapiens* glucosidase, alpha; acid (GAA), transcript variant 1, mRNA" (2006).
GenBank Accession No. X05790, "Human mRNA for alpha-galactosidase A (EC 3.2.1-22)" (1987).
Geoghegan et al., "Site-Directed Conjugation of Nonpeptide Groups to Peptides and Proteins via Periodate Oxidation of a 2-Amino Alcohol. Application to Modification at N-Terminal Serine" *Bioconjugate Chem.* 3:138-146 (1992).
Gottschalk et al., "Folate receptor rriediated DNA delivery into tumor cells: potosomal disruption results in enhanced gene expression" *Gene Ther.* 1:185-191 (1994).
Gregoriadis et al., "Polysialic acids: potential in drug delivery" *FEBS* 315(3):271-276 (Jan. 1993).
Gregoriadis et al., "Polysialylated proteins. An approach to improving enzyme stability and half-life in the blood circulation" *S.T.P. Pharma Sci.* 9(1):61-66 (1999).
Hagihara et al., "Exploration of oligosaccharide-protein interactions in glycoprotein quality control by synthetic approaches" *Chem. Rec.* 6(6):290-302 (2006).
Helenius et al., "Intracellular Functions of N-Linked Glycans" *Science* 291(5512):2364-2369 (Mar. 2001).
Heng et al., "Synthesis of a mannotetraose—the repeating unit of the cell-wall mannans of *Microsporum gypseum* and related species of *Trychophyton*" *J. Carb. Chem.* 20(3-4):285-296 (2001).
Hinman et al., "Preparation and Characterization of Monoclonal Antibody Conjugates of the Calicheamicins: A Novel and Potent Family of Antitumor Antibiotics" *Cancer Res.* 53:3336-3342 (1993).
Hodosi et al., "A Fundamentally New, Simple, Sterospecific Synthesis of Oligosaccharides Containing the β-Mannopyranosyl and β-Rhamnopyranosyl Linkage" *J. Am. Chem. Soc.* 119:2335-2336 (1997).
Hodosi et al., "Glycosylation via locked anomeric configuration: stereospecific synthesis of oligosaccharides containing the β-D-mannopyranosyl and β-L-rhamnopyranosyl linkage" *Carbohydr. Res.* 308:63-75 (1998).
Hoefsloot et al., "Characterization of the human lysosomal α-glucosidase gene" *Biochem. J.* 272:493-497 (1990).
Hojo et al., "Recent Progress in the Solid-phase Synthesis of Glycopeptide" *Current Prot. Peptide Sci.* 1:23-48 (2000).

Horinouchi et al., "Acid sphingomyelinase deficient mice: a model of types A and B Niemann-Pick disease" *Nat. Genet.* 10:288-293 (1995).

International Search Report and Written Opinion issued in International Patent Application No. PCT/US2006/012698; Data of Mailing: Nov. 10, 2006.

International Search Report and Written Opinion issued in International Patent Application No. PCT/US2008/051429; Date of Mailing: Oct. 7, 2008.

Ioannou et al., "Fabry Disease: Preclinical Studies Demonstrate the Effectiveness of α-Galactosidase A Replacement in Enzyme-Deficient Mice" *Am. J. Hum. Genet.* 68:14-25 (2001).

Jeyakumar et al., "Enhanced Survival in Sandhoff Disease Mice Receiving a Combination of Substrate Deprivation Therapy and Bone Marrow Transplantation" *Blood* 97(1):327-329 (Jan. 2001).

Jeyakumar et al., "Glycosphingolipid lysosomal storage diseases: therapy and pathogenesis" *Neuropath. Appl. Neurobiol.* 28:343-357 (2002).

Kakkis et al., "Successful Induction of Immune Tolerance to Enzyme Replacement Therapy in Canine Mucopolysaccharidosis I" *PNAS* 101(3):829-834 (2004).

Kamada et al., "Synthesis of a poly(vinylpyrrolidone-co-dimethyl maleic anhydride) co-polymer and its application for renal drug targeting" *Nat. Blotechnol.* 21:399-404 (Apr. 2003).

Kaneko et al., "New Hydrazone Derivatives of Adriamycin and Their Immunoconjugates—a Correlation between Acid Stability and Cytotoxicity" *Bioconjugate Chem.* 2(3):133-141 (1991).

Kikuchi et al., "Clinical and Metabolic Correction of Pompe Disease by Enzyme Therapy in Acid Maltase-deficient Quail" *J. Clin. Invest.* 101(4):827-833 (1998).

Kim et al., "Mutational spectrum of the iduronate 2 sulfatase gene in 25 unrelated Korean Hunter syndrome patients: identification of 13 novel mutations" *Hum. Mutat.* 21:449-450 (2003).

Kim et al., "Stereoselective direct glycosylation with anomeric hydroxy sugars by activation with phthalic anhydride and trifluoromethanesulfonic anhydride involving glycosyl phthalate intermediates" *J. Am. Chem. Soc.* 130:8537-8547 (2008).

King et al., "Monoclonal Antibody Conjugates of Doxorubicin Prepared with Branched Linkers: A Novel Method for Increasing the Potency of Doxorubicin Immunoconjugates" *Bioconjugate Chem.* 10:279-288 (1999).

Kleinhammer et al., "Synthesis and immunological properties of an artificial antigen with the repeating oligosaccharide unit of *Salmonella illinois* as haptenic group" *Eur. J. Immunol.* 3:834-838 (1973).

Lansmann et al., "Human acid sphingomyelinase. Assignment of the disulfide bond pattern" *Eur. J. Biochem.* 270:1076-1088 (2003).

Lebowitz et al., "Glycosylation-independent targeting enhances enzyme delivery to lysosomes and decreases storage in mucopolysaccharidosis type VII mice" *PNAS* 101(9):3083-3088 (Mar. 2004).

Lecolley et al., "A new approach to bioconjugates for proteins and peptides ("pegylation") utilising living radical polymerisation" *Chem. Commun.* 18:2026-2027 (2004).

Lee et al., "A Biochemical and Pharmacological Comparison of Enzyme Replacement Therapies for the Glycolipid Storage Disorder Fabry Disease" *Glycoblology* 13(4):305-313 (2003).

Lee et al., "Receptor mediated uptake of peptides that bind the human transferrin receptor" *Eur. J. Biochem.* 268:2004-2012 (2001).

Lee et al., "N-Terminal Site-Specific Mono-PEGylation of Epidermal Growth Factor" *Pharm. Res.* 20(5):818-825 (May 2003).

Lees et al., "Versatile and efficient synthesis of protein-polysaccharide conjugate vaccines using aminooxy reagents and oxime chemistry" *Vaccine* 24:716-729 (2006).

Li et al., "Direct Multiplex Assay of Lysosomal Enzymes in Dried Blood Spots for Newborn Screening" *Clin. Chem.* 50(10):1785-1796 (2004).

Liou et al., "Analyses of Variant Acid β-Glucosidases. Effects of Gaucher Disease Mutations" *J. Biol. Chem.* 281(7):4242-4253 (Feb. 2006).

Lisi et al., "Enzyme Therapy. I. Polyethylene Glycol:β-Giucuronidase Conjugates as Potential Therapeutic Agents in Acid Mucopolysaccharidosis" *J. Appl. Biochem.* 4:19-33 (1982).

Litjens et al., "An N-acetylgalactosamine-4-sulfatase mutation (Δ $G_{238}$) results in a severe Maroteaux-Lamy phenotype" *Hum. Mut.* 1(5):397-402 (1992).

Lovering et al., "Mechanistic and Structural Analysis of a Family 31 α-Glycosidase and Its glycosyl-enzyme Intermediate" *J. Biol. Chem.* 280(3):2105-2115 (2005).

MacDermott et al., "Anderson-Fabry disease: clinical manifestations and impact of disease in a cohort of 98 hemizygous males" *J. Med. Genet.* 38:750-760 (2001).

Mann et al., "Endocytosis and targeting of exogenous HIV-1 Tat protein" *EMBO J.* 10(7):1733-1739 (1991).

Marshall et al., "Demonstration of Feasibility of In Vivo Gene Therapy for Gaucher Disease Using a Chemically Induced Mouse Model" *Mol. Ther.* 6(2):179-189 (Aug. 2002).

Matsuzawa et al., "Fabry disease: correlation between structural changes in α-galactosidase, and clinical and biochemical phenotypes" *Hum. Genet.* 7:317-328 (2005).

Mayer et al., "Synthesis of Labeled Glycosyl Phosphatidyl Inositol (GPI) Anchors" *Eur. J. Org. Chem.* 1999(10):2563-2571 (1999).

Mayes et al., "Differential assay for lysosomal α-galactosidases in human tissues and its application to Fabry's disease" *Clin. Chim. Acta* 112:247-251 (1981).

Medin et al., "Correction in trans for Fabry disease: Expression, secretion and uptake of α-galactosidase A in patient-derived cells driven by a high-titer recombinant retroviral vector," *Proc. Natl. Acad. Sci. USA* 93:7917-7922 (1996).

Menander-Huber et al., "Orgotein, the Drug Version of Bovine Cu-Zn Superoxide Dismutase II, A Summary Account of Clinical Trials in Man and Animals" in *Superoxide and Superoxide Dismutases*. A.M. Michelson et al. (eds.), Academic Press, 1977; pp. 537-549.

Michelson et al., "Production of Superoxide by Metal Ions" in *Superoxide and Supeoxide Dismutases*. A.M. Michelson et al. (eds.), Academic Press, 1977; pp. 116-125.

Minko et al., "Molecular Targeting of Drug Delivery Systems to Cancer" *Current Drug Targets* 5:389-406 (2004).

Mitchell et al., "Polyarginine enters cells more efficiently than other polycationic homopolymers" *J. Peptide Res.* 56:318-325 (2000).

Mizukami et al., "Systemic inflammation in glucocerebrosidase-deficient mice with minimal glucosylceramide storage" *J. Clin. Invest.* 109:1215-1221 (2002).

Munier-Lehmann et al., "Re-expression of the Mannose 6-Phosphate Receptors in Receptor-deficient Fibroblasts" *J. Biol. Chem.* 271(25):15166-15174 (1996).

Murray et al., "Cellular and Tissue Distribution of Intravenously Administered Agalsidase Alfa" Author manuscript [online]: http://www.ncbi.nlm.nih.gov/pmc/articles/PMC1839873/pdf/nihms19304.pdf. Final publication in: *Mol. Genet. Metab.* 90(3):307-312 (2007).

Murunganandam et al., "Selection of phage-displayed llama single-domain antibodies that transmigrate across human blood-brain barrier endothelium" *FASEB J.* 16:240-242(2002).

Nicolaou et al., "New Synthetic Technology for the Stereocontrolled Construction of 1,1'-Disaccharides and 1,1':1",2-Trisaccharides. Synthesis of the FG Ring System of Everninomicin 13,384-1" *J. Am. Chem. Soc.* 119:9057-9058 (1997).

Nieman et al., "Family 39 α-L-iduronidases and β-D-xylosidases react through similar giycosyl-enzyme intermediates: identification of the human iduronidase nucleophile" *Biochemistry* 42(26):8054-8065 (Jul. 2003).

Office Action issued in U.S. Appl. No. 12/523,631, mailed Feb. 21, 2012.

Ohkuma et al., "Fluorescence probe measurement of the intralysosomal pH in living cells and the perturbation of pH by various agents" *Proc. Natl. Acad. Sci. USA* 75(7):3327-3331 (1978).

Ohshima et al., "α-Galactosidase A deficient mice: A model of Fabry disease" *Proc. Natl. Acad. Sci. USA* 94:2540-2544 (Mar. 1997).

Olson et al., "Structure of uPAR, plasminogen, and sugar-binding sites of the 300 kDa mannose 6-phosphate receptor" *EMBO J.* 23:2019-2028 (2004).

Olson et al., "Structural Basis for Recognition of Phosphorylated High Mannose Oligosaccharides by the Cation-dependent Mannose 6-Phosphate Receptor" *J. Biol. Chem.* 274(42):29889-29886 (Oct. 1999).

Olson et al., "Twists and Turns of the Cation-dependent Mannose 6-Phosphate Receptor" *J. Biol. Chem.* 277(12):10156-10161 (Mar. 22, 2002).

Olson et al., "The N-terminal Carbohydrate Recognition Site of the Cation-independent Mannose 6-Phosphate Receptor" *J. Biol. Chem.* 279(32):34000-34009 (Aug. 2004).

Orr et al., "Synthetic Concanavalin A Receptors and Erythrocyte Agglutination" *Nature* 272:722-725 (1978).

Papisov et al., "Hydrophilic Polyals: Biomimetic Biodegradable Stealth Materials for Pharmacology and Bioengineering" Abstract, 226th American Chemical Society National Meeting, New York, NY, Sep. 7-11, 2003, 3 pages.

Papisov et al., "Semisynthetic Hydrophilic Polyals" *Biomacromolecules* 6:2659-2670 (2005).

Papisov, "Acyclic polyacetals from polysaccharides" *ACS Symposium Series* 786:301-314 (2001).

Pekari et al., "Synthesis of the fully phosphorylated GPI anchor pseudohexasaccharide of *Toxoplasma gondii*" *J. Org. Chem.* 66:7432-7442 (2001).

Peters et al., "Phylogenetic Conservation of Arylsulfatases. cDNA Cloning and Expression of Human Arylsulfatase B" *J. Biol. Chem.* 265(6):3374-3381 (Feb. 1990).

Poznansky et al., "α-1,4-Glucosidase-albumin polymers: in vitro properties and advantages for enzyme replacement therapy" *Can. J. Physiol. Pharmacol.* 58:322-325 (1980).

Poznansky et al., "Insulin Carrier Potential for Enzyme and Drug Therapy" *Science* 223:1304-1306 (1984).

Prince et al., "Lipoprotein Receptor Binding, Cellular Uptake, and Lysosomal Delivery of Fusions between the Receptor-associated Protein (RAP) and α-L-Iduronidase or Acid α-Glucosidase" *J. Biol. Chem.* 279(33):35037-35046 (Aug. 2004).

Rempel et al., "A homology model for human α-L-iduronidase: insights into human disease" *Mol. Genet. Metab.* 85:28-37 (2005).

Rodriguez et al., "A Strategy for the Chemoselective Synthesis of O-Linked Glycopeptides with Native Sugar-Peptide Linkages" *J. Am. Chem.* 119(4):9905-9906 (1997).

Rodwell et al., "Site-specific covalent modification of monoclonal antibodies: in vitro and in vivo evaluations" *Proc. Natl. Acad. Sci. USA* 83:2632-2636 (1986).

Roussele et al., "New Advances in the Transport of Doxorubicin through the Blood-Brain Barrier by a Peptide Vector-Mediated Strategy" *Mol. Pharmacol.* 57:679-686 (2000).

Rudinger, "Characteristics of the amino acids as components of a peptide hormone sequence" in *Peptide Hormones*. J.A. Parsons (ed.) Baltimore, MD: Univ. Park Press, 1976; pp 1-7.

Schnyder et al., "Targeting of skeletal muscle in vitro using biotinylated immunoliposomes" *Biochem. J.* 377:61-67 (2004).

Schuchman et al., "Human arylsulfatase B: MOPAC cloning nucleotide sequence of a full-length cDNA and regions of amino acid identity with arylsulfases A and C" *Genomics* 6(1):149-158 (1990).

Schwarze et al., "In Vivo Protein Transduction: Delivery of a Biologically Active Protein into the Mouse" *Science* 285:1569-1572 (Sep. 1999).

Scott et al., "Structure and Sequence of the human α-L-iduronidase gene" *Genomics* 13:1311-1313 (Aug. 1992).

Scott et al., "Human α-L-iduronidase: cDNA isolation and expression" *Proc. Natl. Acad. Sci USA* 88:9695-9699 (Nov. 1991).

Scott et al., "Molecular genetics of mucopolysaccharidosis type I: diagnostic clinical and biological implications" *Hum. Mutat.* 6(4):288-302 (1995).

Seeberger et al., "Synthesis and medical application sof oligosaccharides" *Nature* 446(7139):1046-1051 (Apr. 2007).

Seeberger et al., "Automated synthesis of oligosaccharides as a basis for drug discovery" *Nat. Rev. Drug Discov.* 4(9):751-763 (2005).

Seto et al., "A model of the acid sphingomyelinase phosphoesterase domain based on its remote strucutal homolog purple acid phosphatase" *Protein Sci.* 13:3172-3186 (2004).

Shen et al,. "Conjugation of poly-L-lysine to albumin and horseradish peroxidase: A novel method of enhancing the cellular uptake of proteins" *Proc. Natl. Acad. Sci. USA* 75:1872-1878 (1978).

Srivastava et al., "Synthesis of β-D-Mannopyranosides and Regioselective O-Alkylation of Dibutylstannylene Complexes" *Tetrahedron Letters* 20(35):3269-3272 (1979).

Sukegawa-Hayasaka et al., "Effect of Hunter Disease (Mucopolysaccharidosis Type II) Mutations on Molecular Phenotypes of Iduronate-2-Sulfatase: Enzymatic Activity, Protein Processing and Structural Analysis" *J. Inherit. Metab. Dis.* 29(6):755-761 (2005).

Takahashi et al., "Acid Sphingomyelinase: Relation of [99]Lysine Residue on the Ratio of Intracellular to Secreted Enzyme Activity" *Tokohu J. Exp. Med.* 206:333-340 (2005).

Tang et al., "Novel Approach to the Study of the Antigenicities and Receptor Functions of Carbohydrate Chains of Glycoproteins" *Biochem. Biophys. Res. Commun.* 132(2):474-480 (1985).

Torchilin, "Drug Targeting" *Eur. J. Pharm. Sci.* 11(Suppl. 2):S81-S91 (2000).

Umpathysivam et al., "Determination of Acid α-Glucosidase Activity in Blood Spots as a Diagnostic Test for Pompe Disease" *Clin. Chem.* 47(6):1378-1383 (2001).

Van Diggelen et al., "A new fluorimetric enzyme assay for the diagnosis of Niemann-Pick A/B with specificity of natural sphingomyelinase substrate" *J. Inherit. Metab. Dis.* 28:733-741 (2005).

Voznyi et al., "A fluorimetric enzyme assay for the diagnosis of MPS II (Hunter disease)" *J. Inherit. Metab. Dis.* 24:675-680 (2001).

Wadhwa et al., "Receptor Mediated Glycotargeting" *J. Drug Targeting* 11(5):255-268 (2003).

Wagner et al., "Coupling of adenovirus to transferrin-polylysine/DNA complexes greatly enhances receptor-mediated gene delivery and expression of transfected genes" *Proc. Natl. Acad. Sci. USA* 89:6099-6103 (Jul. 1992).

Wang et al., "Addition of the keto functional group to the genetic code of *Escherichia coli*" *PNAS* 100(1):56-61 (Jan. 2003).

Wang et al., "Single-Chain Fv with manifold N-glycans as bifunctional scaffolds for immunomolecules" *Protein Eng.* 11(12):1277-1283 (1998).

Wender et al., "The design, sythesis, and evaluation of molecules that enable or enhance cellular uptake: Peptoid molecular transporters" *PNAS* 97(24):13003-13008 (2000).

Wieder et al., "Enzyme Therapy: II, Effect of Covalent Attachment of Polyethylene Glycol on Biochemical Parameters and Immunological Determinants of β-Glucosidase and α-Galactosidase" *J. Appl. Biochem.* 5:337-347 (1983).

Wilson et al., "Sequence of the Human Iduronate 2-Sulfatase (IDS) Gene" *Genomics* 17:773-775 (1993).

Wilson et al., "Hunter syndrome: Isolation of an iduronate-2-sulfatase cDNA clone and analysis of patient DNA" *Proc. Natl. Acad. Sci. USA* 87:8531-8535 (Nov. 1990).

Yamazaki et al., "Synthesis of α-D-Man$p$-(1→3)-[β-D-Glc$p$NAc-(1→4)]-[α-D-Man$p$-(1→6)]-β-D-Man$p$-(1→4)-β-D-Glc$p$NAc-(1→4)-[α-L-Fuc$p$-(1→6)]-D-Glc$p$NAc, a core glycoheptaose of a 'bisected' complex-type glycan of glycoproteins" *Carb. Res.* 201:31-50 (1990).

Yamazaki et al., "Endogenous Lectins as Targets for Drug Delivery" *Adv. Drug Deliv. Rev.* 43:225-244 (2000).

Yurkovetskiy et al., "Fully Degradable Hydrophilic Polyals for Protein Modification" *Biomacromolecules* 6:2648-2658 (2005).

Zalipsky et al., "Hydrazide Derivatives of Poly(ethylene glycol) and Their Bioconjugates" *Poly(ethylene glycol) Chemistry and Biological Applications* 680:318-341(1997).

Zara et al., "A Carbohydrate-Directed Heterobifunctional Cross-Linking Reagent for the Synthesis of Immunoconjugates" *Anal. Biochem.* 194:156-162 (1991).

Zhou et al., "Strategies for Neoglycan Conjugation to Human Acid α-Glucosidase" *Bioconj. Chem.* 22:741-751 (2011).

Zhu et al., "Glycoengineered Acid α-Glucosidase with Improved Efficacy at Correcting the Metabolic Aberrations and Motor Function Deficits in a Mouse Model of Pompe Disease" *Mol. Ther.* 17(6):954-963 (Jun. 2009).

* cited by examiner

METHODS FOR INTRODUCING MANNOSE 6-PHOSPHATE AND OTHER OLIGOSACCHARIDES ONTO GLYCOPROTEINS AND ITS APPLICATION THEREOF

PRIORITY INFORMATION

This application is a continuation of U.S. application Ser. No. 10/943,893, filed Sep. 20, 2004 now U.S. Pat. No. 7,723,296, which is a continuation-in-part of U.S. patent application Ser. No. 10/051,711, filed Jan. 17, 2002 (now U.S. Pat. No. 7,001,994), which claims the benefit of priority of U.S. provisional patent application No. 60/263,078, filed Jan. 18, 2001, all of which are incorporated herein by reference in their entirety.

BACKGROUND OF THE INVENTION

The present invention relates in general to methods for introducing new oligosaccharides to glycoproteins, and more specifically, to novel methods for conjugating highly phosphorylated mannopyranosyl oligosaccharide derivatives to glycoproteins to form compounds containing mannose-6-phosphate (M6P) for use in medical methods of treatment, and to the compounds thereby produced.

Carbohydrates on glycoproteins play important biological functions in bio-organisms. Well-characterized examples include the selectin-carbohydrate interaction involved in intercellular cell adhesion and sperm/egg interaction (see, e.g., C. G. Gahmberg et al., 27 APMIS SUPPL. 39 (1992)), and the mannose 6-phosphate (M6P) dependent lysosomal enzyme targeting pathway (see, e.g., S. Kornfeld and I. Mellman, 5 ANNUAL REVIEW OF CELL BIOLOGY 483 (1989)). To facilitate study of the complex functions of carbohydrate structures on glycoproteins, both enzymatic and chemical methods have been developed to remove the carbohydrate glycans from glycoproteins for analysis. A variety of conjugation methods have also been developed to conjugate defined carbohydrates to proteins and then analyze their possible biological functions. The most commonly used conjugation approach involves the use of omega-amino groups of lysine residues. Reactions of amino groups of proteins with compounds such as N-hydroxysuccinimide ester or isothiocyanate derivatives are widely used. Reductive amination, on the other hand, is most commonly used for carbohydrate conjugation to proteins. For example, in the analysis of lysosomal enzyme targeting, coupling of M6P or phosphopentamannose to bovine serum albumin has been achieved through reductive amination (H. Tomoda et al., 213 CARBOHYDR. RES. 37 (1991); T. Baba et al., 177 CARBOHYDR. RES. 163 (1988)), leading to significant insights regarding the M6P receptor binding to lysosomal enzymes through these M6P conjugated glycoproteins. Reductive amination involves covalently linking the reducing ends of oligosaccharides to amino acid residues in proteins containing free amines (such as lysines), to first form unstable Schiff bases which are then reduced by cyanoborohydride to stable imine bonds.

However, these known conjugation methods are limited in that they are not specific in terms of the amino acid residues involved, and require the direct linkage of chemical conjugates or carbohydrates to amino acid residues, which may cause a change in protein conformation and destroy the biological activity of proteins. For example, when antibody IgG is coupled to various chemical conjugates through amino acid groups, the antibody IgG often loses its immunological activity (D. J. O'Shannessy and R. H. Quarles, 7 J. OF APPL. BIOCHEM. 347, (1985); T. I. Ghose et al., 93 METHODS IN ENZYMOLOGY 280 (1983)). In addition, reductive amination requires high pH and a reductive reagent that may also reduce any disulfide bonds in a protein, thus potentially destroying biological activity.

A more specific approach to introduce certain chemical conjugates onto glycoproteins has been described and involves covalent bond formation between carbonyl (aldehyde) groups generated by mild oxidation of carbohydrates with periodate or galactose oxidase (G. Avigad et al., 237 J. BIOL. CHEM. 2736 (1962)) and chemical compounds containing carbonyl-reactive groups. This approach has been used for in vitro attachment of mono- and oligosaccharides to cell surface glycoconjugates of living cells with glycosylhydrazines (M. Tolvanen and C. G. Gahmberg, 261(2) J. BIOL. CHEM. 9546 (1986); C. G. Gahmberg and M. Tolvanen, 230 METHODS IN ENZYMOLOGY 32 (1994)). Other applications include conjugation of biotin or avidin to glycoproteins with biotin-hydrazide or avidin-hydrazide (Bayer et al., 161 ANALYTICAL BIOCHEMISTRY 123 (1987); Bayer et al., 170 ANALYTICAL BIOCHEMISTRY 271 (1988); M. Wilchek and E. A. Bayer, 128 METHODS IN ENZYMOLOGY 429 (1987)), antibody IgG conjugation for immunodetection (O'Shannessy et al., 8 IMMUNOLOGY LETTERS 273 (1984); D. J. O'Shannessy and R. H. Quarles, 7 J. OF APPL. BIOCHEM. 347 (1985)) and cancer immunotherapy (J. Singh Kralovec et al., 29 CANCER IMMUNOLOGY THERAPY 293 (1989); G. R. Braslawsky et al., 33 CANCER IMMUNOLOGY THERAPY 367 (1991)). In these examples, the glycoproteins are treated by mild oxidation with periodate to generate aldehyde groups that then react with hydrazide derivatives. One advantage of this approach for conjugation is that the linkage is through the carbohydrates on the glycoproteins instead of directly involving the protein backbone, thus avoiding inactivation of the glycoproteins' biological activity. Antibodies modified in such a way always retain activity (D. J. O'Shannessy et al., 8 IMMUNOLOGY LETTERS 273 (1984); D. J. O'Shannessy and R. H. Quarles, 7 J. OF APPL. BIOCHEM. 347 (1985)). In addition, both the oxidation and the covalent bond formation steps are nearly quantitative, and reaction conditions are very mild, thus helping retain the biological activity of the proteins. Retention of biological activity is critical when the modified glycoproteins are to be used for therapeutic purposes.

Lysosomal storage disease describes a class of over 40 genetic disorders (see, e.g., Holton, J. B., THE INHERITED METABOLIC DISEASES 205-242 ($2^{nd}$ ed. 1994); Scriver et al., 2 THE METABOLIC BASIS OF INHERITED DISEASE ($7^{th}$ ed. 1995)), each resulting from a deficiency of a particular lysosomal enzyme, usually as a result of genetic mutation. Lysosomal enzymes are required to break down protein, glycolipid and carbohydrate metabolites within the lysosomes of cells. When one or more of these enzymes are defective in affected individuals due to inherited mutations, lysosomes in cells of affected individuals accumulate a subset of undigested substrates, largely liposaccharides and carbohydrates as storage materials that are unable to be digested by the defective enzymes. For example, in Gaucher disease, deficiency of beta-glucocerebrosidase causes the accumulation of glucosylceramide; in Fabry disease, the defective alpha-galactosidase A results in accumulation of globotriaosylceremide; in Pompe disease, lack of acid alpha-glucosidase causes accumulation of glycogen alpha 1-4 linked oligosaccharides and in Tay-Sachs disease, deficiency of beta-N-acetyl-hexosaminidase leads to accumulation of GM2 ganglioside. Clinically, patients with these syndromes show a variety of symptoms associated with the accumulation of these storage material in the lysosomes, which eventually affect the normal function of the cells or tissues that result in dysfunction of organs within the human body. The severity of the disease varies with the residual enzyme activity, in severe cases, death can occur early in life.

Lysosomal enzymes, like other secretory proteins, are synthesized and co-translationally translocated into the lumen of the endoplasmic reticulum, where post-translational carbohydrate modification occurs. However, while in transit through the Golgi, they are segregated from the other secretory proteins by specifically acquiring the M6P recognition marker generated by the sequential actions of two enzymes. The first enzyme, UDP-N-acetylglucosamine: Lysosomal-enzyme N-Acetylglucosamine-1-phosphotransferase, transfers the N-acetylglucosamine-1-phosphate to one or more mannose residues on lysosomal enzymes to give rise to phosphodiester intermediates, and the second enzyme, N-acetylglucosamine-1-phosphodiester alpha-N-acetylglucosaminidase, removes the N-acetylglucosamine from the phosphodiester to expose the M6P. Once the lysosomal enzymes with the M6P recognition marker reach the trans-Golgi-network, they are recognized by two specific receptors, the cation-independent mannose 6-phosphate receptor (CI-MPR) and the cation-dependent mannose 6-phosphate receptor (CD-MPR). These receptors with their ligands of lysosomal enzymes are sequestered into clathrin-coated vesicles formed on the trans-Golgi network and transported to endosomes, where the lysosomal enzymes are dissociated from the receptors by the low pH in endosomes and eventually delivered to lysosomes. Some of the lysosomal enzymes are secreted, however, they are captured by binding to the CI-MPR on the cell surface and internalized by the AP-2 mediated clathrin-coated vesicles. Thus, the M6P dependent pathway is the main targeting pathway for lysosomal enzymes, though the M6P independent targeting pathways have been proposed for a few lysosomal enzymes and in certain cell types (see Kornfeld and Mellman, supra).

With the complete elucidation of the lysosomal enzyme targeting pathway and the discovery of lysosomal enzyme deficiencies as the primary cause of lysosomal storage diseases, attempts have been made to treat patients having lysosomal storage diseases by intravenous administration of the missing enzyme, i.e., enzyme replacement therapy, where the injected enzymes are expected to be taken up by target cells through receptor-mediated endocytosis and delivered to lysosomes. Animal models and some clinical trials of enzyme replacement therapy have offered positive results. However, for lysosomal diseases other than Gaucher disease, some evidence suggest that enzyme replacement therapy is most effective when the enzyme being administered has M6P, so that the enzymes can be taken up efficiently by the target cells through the cell surface associated CI-MPR-mediated endocytosis. Gaucher disease, caused by the deficiency of beta-glucocerebrosidase, is an exception because beta-glucocerebrosidase is among the few lysosomal enzymes that are targeted by the M6P independent pathway (see Kornfeld and Mellman, supra). Targeting of beta-glucocerebrosidase for Gaucher disease enzyme replacement therapy to macrophage cells is mediated by remodeling its carbohydrate to expose the core mannose, which binds to the mannose receptor on macrophage cell surface.

While enzyme replacement therapy (ERT) appears promising, supplies of the required enzymes are limited. Lysosomal enzymes can, in theory, be isolated from natural sources such as human placenta or other animal tissues. However, large-scale production of sufficient quantities of enzymes for therapeutic administration is difficult. Further, due to the degradation of carbohydrates in lysosomes, enzymes purified from tissues do not contain significant amounts of M6P. Alternative approaches include use of recombinant protein expression systems, facilitated by large-scale cell culture or fermentation. For example, lysosomal enzymes have been expressed in Chinese hamster ovary (CHO) cells (V. A. Ioannou et al., 119(5) J. Cell Biol. 1137 (1992); E. D. Kakkis et al., 5 Protein Expression Purification 225 (1994)), insect cells (Y. Chen et al., 20(2) Protein Expr. Purif. 228 (2000)), and in transgenic animals or plants (A. G. Bijvoet et al., 8(12) Hum. Mol. Genet. 2145 (1999)). However, lysosomal enzymes purified from recombinant expression systems are also often not well phosphorylated and the extent of M6P phosphorylation varies considerably with different enzymes. Alpha-galactosidase A expressed in CHO cells contains about 20% of phosphorylated enzymes, but only 5% are bisphosphorylated, which is the high-uptake form (F. Matsuura et al., 8(4) Glycobiology 329 (1998)). Alpha-N-acetylglucosaminidase expressed in CHO cells is almost completely lacking M6P phosphorylation (K. Zhao and E. F. Neufeld, 19 Protein Expr. Purif. 202 (2000)). In addition, recombinant proteins expressed in plants, insect cells or the methotrophic yeast pichia pastoris do not have any M6P phosphorylation because such cells do not have the M6P targeting pathway.

Lysosomal enzymes lacking in M6P phosphorylation compete poorly for receptor-mediated endocytic uptake by target cells and are thus of limited efficacy in enzyme replacement therapy. More specifically, poorly phosphorylated enzymes are effectively removed by the mannose receptor (M. E. Taylor et al., 252 Am. J. Physiol. E690 (1987)) and asiologlycoprotein receptor in liver (Ashwell and Harford, 51 Ann. Rev. Biochem 531 (1982)), which can remove most of any administered lysosomal enzymes within a very short period of time.

Against this background, a strong need exists for improved, efficient approaches to phoshorylate lysosomal enzymes, and particularly for methods to modify lysosomal enzymes with M6P. In addition, a need exists for modifying lysosomal enzymes to a high uptake, bisphosphorylated form. Such modified enzymes would be particularly useful for enhancing the efficacy of enzyme replacement therapy for lysosomal storage disease.

BRIEF SUMMARY OF THE INVENTION

Methods of creating neoglycoproteins are provided that increase the cellular uptake of lysosomal enzymes and other glycoproteins by covalently attaching oligosaccharide compositions to oxidized glycans of the glycoproteins through covalent bonds.

Thus, in one embodiment, the invention is directed toward a method for coupling a highly phosphorylated mannopyranosyl oligosaccharide compound to a glycoprotein having at least one glycan, the method comprising derivatizing the highly phosphorylated mannopyranosyl oligosaccharide compound with a chemical compound containing a carbonyl-reactive group; oxidizing the glycoprotein having the at least one glycan to generate at least one aldehyde group on the glycoprotein; and reacting the oxidized glycoprotein having at least one glycan with the derivatized highly phosphorylated mannopyranosyl oligosaccharide compound to form a new compound having a hydrazone bond. The glycoprotein in one embodiment is a lysosomal enzyme.

In one embodiment of the methods, the highly phosphorylated mannopyranosyl oligosaccharide compound contains at least one mannose 6-phosphate group, such as a compound having the formula 6-P-$M_n$-R wherein:

M is a mannose or mannopyranosyl group;

P is a phosphate group linked to the C-6 position of M;

R comprises a chemical group containing at least one carbonyl-reactive group; and n is an integer from 1-15, wherein if n>1, $M_n$ are linked to one another by alpha (1,2), alpha (1,3), alpha (1,4), or alpha (1,6).

Thus, the highly phosphorylated mannopyranosyl oligosaccharide compound includes compounds such as M6P, phosphopentamannose derived from Hansenula holstii O-phosphomannan, and 6-P-M-(alpha 1,2)-M(alpha 1,2)-M.

In another embodiment of the methods, the highly phosphorylated mannopyranosyl oligosaccharide compound comprises a compound having the formula $(6\text{-}P\text{-}M_x)_m L_n\text{-}R$ wherein:

M is a mannose or mannopyranosyl group;

L is a mannose or other hexose or other chemical groups;

P is a phosphate group linked to the C-6 position of M;

R comprises a chemical group containing at least one carbonyl-reactive group;

m is an integer from 2-3;

n is an integer from 1-15, wherein if n>1, $M_n$ are linked to one another by alpha (1,2), alpha (1,3), alpha (1,4), or alpha (1,6); and x is an integer from 1-15.

Thus, the highly phosphorylated mannopyranosyl oligosaccharide compound includes biantennary mannopyranosyl oligosaccharide compounds containing bis-M6P and triantennary mannopyranosyl oligosaccharide compounds containing bis-M6P or tri-M6P.

In one embodiment of the methods, the highly phosphorylated mannopyranosyl oligosaccharide compound can be replaced with other oligosaccharide compositions containing terminal hexoses, such as, for example, a galactose, a mannose, N-acetylglucosamine, or a fucose, which can bind to different carbohydrate-binding receptors other than CI-MPR.

In another embodiment of the methods, the chemical compound containing carbonyl-reactive group includes any compound that reacts with carbonyl groups to form a hydrazone bond. Such compounds include hydrazines, hydrazides, aminooxyls, and semicarbozides and the like.

In addition, the methods further encompass reducing the compound having a hydrazone bond with a reducing agent such as cyanoborohydride to form a compound having an imine bond.

The invention is further directed toward chemical compounds produced by coupling a first chemical compound having at least one carbonyl group (aldehyde or ketone) to a second chemical compound comprising a phosphorylated mannopyranosyl oligosaccharide derivative, according to the coupling methods described and herein, i.e., by derivatizing the highly phosphorylated mannopyranosyl oligosaccharide compound with a chemical compound containing a carbonyl-reactive group; and reacting to the first chemical compound having at least one carbonyl group with the derivatized highly phosphorylated mannopyranosyl oligosaccharide compound to form a new compound having a hydrazone bond. Such compounds include antiviral compounds and gene targeting delivery agents.

In another embodiment, the invention is directed toward methods of treating lysosomal storage disease in a subject in need thereof, the methods including administering to the subject an effective amount of a glycoprotein coupled according to the methods described herein to a second chemical compound comprising a highly phosphorylated mannopyranosyl oligosaccharide derivative containing at least one mannose 6-phosphate group. Lysosomal storage diseases that are treated with a glycoprotein modified according to the methods described herein include Fabry disease, Pompe disease, and others (for a complete list, see J. B. Holton, THE INHERITED METABOLIC DISEASES 205-242 (2d ed. 1994); C. R. Scriver et al., 2 THE METABOLIC BASIS OF INHERITED DISEASE ($7^{th}$ ed. 1995)).

The present methods couple highly phosphorylated mannopyranosyl oligosaccharides containing M6P, to glycoproteins, so that cellular uptake of such glycoproteins is enhanced without destroying their biological activity. As such, the methods and compounds produced thereby are especially useful where in medical treatment methods that benefit from enhanced uptake forms of glycoproteins, such as in enzyme replacement therapy for the treatment of lysosomal storage diseases.

BRIEF DESCRIPTION OF THE DRAWINGS

FIG. 15A shows in vitro uptake of rhGAA (closed circles) and neo-rhGAA (closed squares) into L6 myoblasts, as measured by GM activity in cell lysates following treatment with rhGAA or neo-rhGAA. FIG. 15B depicts a bar graph showing the results of an in vitro uptake experiment in macrophages, treated either with rhGAA or neo-rhGAA, and further in presence or absence of M6P and/or mannan. As in the case of myoblasts, in vitro uptake was measured by assaying for GM activity in cell lysates.

DETAILED DESCRIPTION OF THE INVENTION

Figure 1:
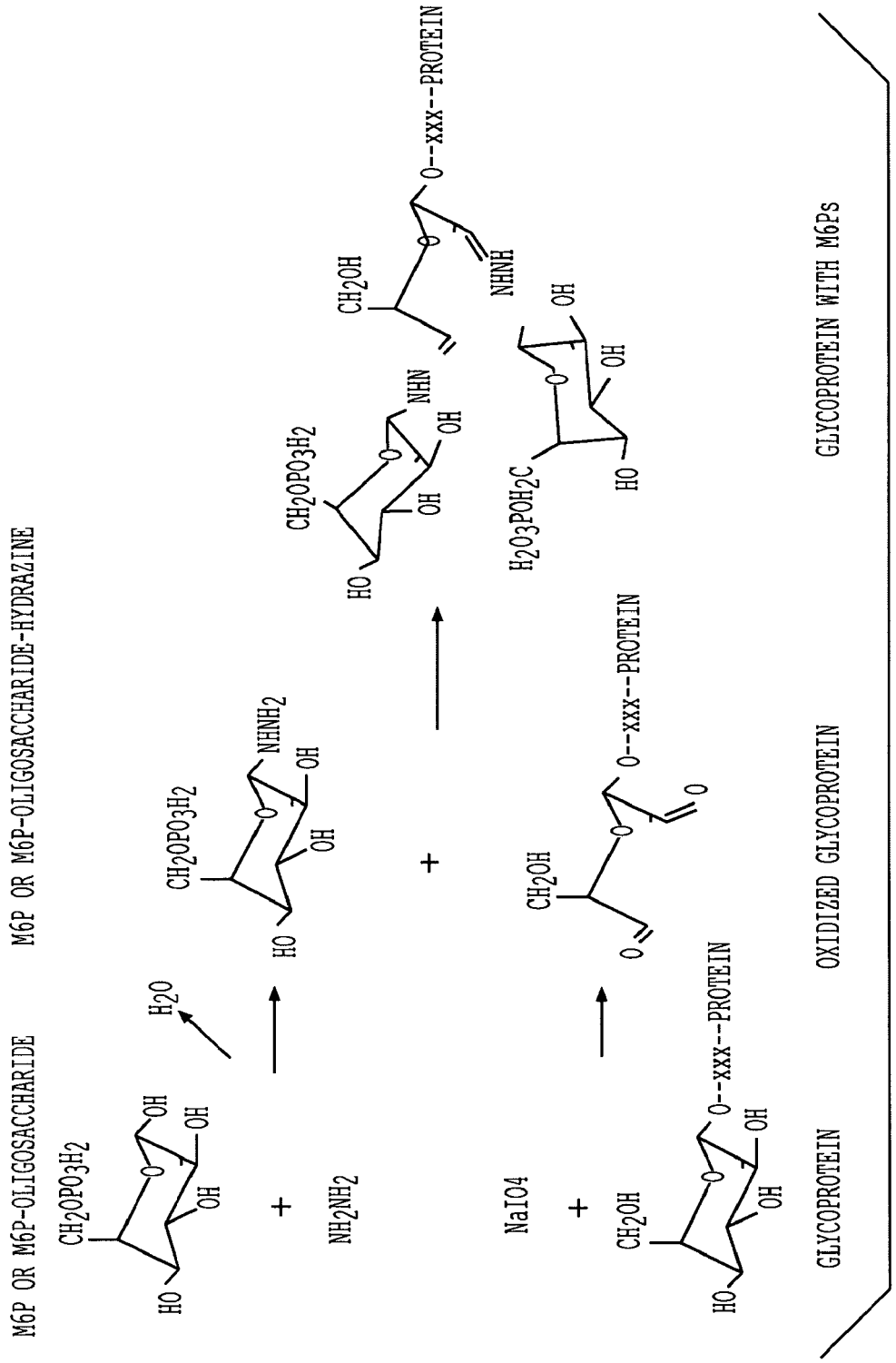
FIG. 1 is a schematic representation of a conjugation method.

The present methods couple highly phosphorylated mannopyranosyl oligosaccharides containing M6P to glycoproteins, such as, for example, avidin and lysosomal enzymes beta-glucuronidase and acid alpha-glucosidase, without destroying their biological activity. The present methods thus provide a novel approach to introduce highly phosphorylated mannosyloligosaccharide derivatives to lysosomal enzymes and other glycoproteins. In exemplary embodiments, the methods and compounds described herein are useful for modifying lysosomal enzymes produced by recombinant protein expression system with M6P, thus to enhance the efficacy of enzyme replacement therapy of lysosomal storage diseases.

As used herein, the term "highly phosphorylated" refers to a characteristic of oligosaccharides that are coupled to glycoproteins or to other compounds according to the methods described herein, wherein the oligosaccharides contain at least one M6P group and, in an exemplary embodiment, two or more M6P groups.

As used herein, the term "effective" refers to a characteristic of an amount of a compound produced according to the methods of the present invention, wherein the amount of the compound has the effect of preventing or reducing a deficiency of a lysosomal enzyme in a subject. The lysosomal enzyme deficiency is, for example, the result of a genetic mutation in a human that produces a lysosomal storage disease. Such diseases include, for example, Gaucher disease wherein a deficiency of beta-glucocerebrosidase results in the accumulation of glucosylceramide, Fabry disease wherein a deficiency of alpha-galactosidase A results in accumulation of globotriaosylceremide, Pompe disease wherein a deficiency of acid alpha-glucosidase results in accumulation of glycogen alpha 1-4-linked oligosaccharides, and Tay-Sachs disease wherein a deficiency of beta-N-acetyl-hexosaminidase leads to accumulation of GM2 ganglioside, and other diseases including Hurler or Hurler-Scheie disease, Krabbe disease, Metachromatic leukodystrophy, Hunter disease, Sanfilippo A and B disease, Morquip A disease, and Maroteaux-Lamy disease and other diseases (see Holton, J. B., 1994, THE INHERITED METABOLIC DISEASES, 2$^{nd}$ Edition; Scriver et al., 1995, THE METABOLIC BASIS OF INHERITED DISEASE, Volume 2, 7$^{th}$ Edition, which are herein incorporated by reference).

Thus, in an exemplary embodiment, a method for coupling a highly phosphorylated mannopyranosyl oligosaccharide compound to a glycoprotein having at least one glycan includes derivatizing the highly phosphorylated mannopyranosyl oligosaccharide compound with a chemical compound containing a carbonyl-reactive group; oxidizing the glycoprotein having the at least one glycan to generate at least one aldehyde group on the glycoprotein; and reacting the oxidized glycoprotein with the derivatized highly phosphorylated mannopyranosyl oligosaccharide compound to form a new compound having a hydrazone bond. Oxidizing the glycoprotein having the at least one glycan is accomplished using, for example, periodate or galactose oxidase.

The glycoprotein having the at least one glycan is, for example, a glycoprotein such as a lysosomal enzyme. The glycoprotein can be derived from a variety of sources. In the case of lysosomal enzymes, natural sources include human placenta and other animal tissues. Alternatively, lysosomal enzymes that are especially useful for modification according to the present methods are produced by recombinant protein expression systems, including yeast, mammalian cells, insect cells, plant cells and transgenic animals or plants.

The chemical compound containing the carbonyl-reactive group is any compound that reacts with carbonyl groups to form a hydrazone bond. Suitable such compounds include, for example, hydrazine, hydrazide, aminooxyl, and semicarbozide and the like.

In one embodiment, the highly phosphorylated mannopyranosyl oligosaccharide compound contains at least one mannose 6-phosphate group, such as an oligosaccharide of the formula 6-P-M$_n$-R wherein:

M is a mannose or mannopyranosyl group;
P is a phosphate group linked to the C-6 position of M;
R comprises a chemical group containing at least one carbonyl-reactive group; and
n is an integer from 1-15, wherein if n>1, M$_n$ are linked to one another by alpha (1,2), alpha (1,3), alpha (1,4), or alpha (1,6).

Thus, the highly phosphorylated mannopyranosyl oligosaccharide compound includes compounds such as M6P, phosphopentamannose derived from Hansenula holstii O-phosphomannan, and 6-P-M-(alpha 1,2)-M(alpha 1,2)-M.

In an exemplary embodiment, the oligosaccharides are those biantennary and triantennary oligosaccharides that have the formula of (6-P-M$_x$)$_m$L$_n$-R wherein:

M is a mannose or mannopyranosyl group;
L is a mannose or other hexose or other chemical groups;
P is a phosphate group linked to the C-6 position of M;
R comprises a chemical group containing at least one carbonyl-reactive group;
m is an integer from 2-3;
n is an integer from 1-15, wherein if n>1, M$_n$ are linked to one another by alpha (1,2), alpha (1,3), alpha (1,4), or alpha (1,6); and
x is an integer from 1-15.

Thus, the highly phosphorylated mannopyranosyl oligosaccharide compound includes biantennary mannopyranosyl oligosaccharide compounds containing bis-M6P and triantennary mannopyranosyl oligosaccharide compounds containing bis-M6P or tri-M6P. An exemplary such compound is

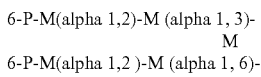

which has about 100 times higher affinity to the MPRs than the phosphopentamannose and M6P, and about 10 times higher affinity to the MPRs than the bi- or tri-oligosaccharides bearing a terminal M6P (Distler et al. 1991).

Alternatively, the highly phosphorylated mannopyranosyl oligosaccharide compound can be replaced with oligosaccharides containing terminal hexoses, such as a galactose, a mannose, N-acetylglucosamine, or a fucose, which can bind to different carbohydrate-binding receptors other than CI-MPR.

In addition, methods include the further step of reducing a compound having a hydrazone bond with a reducing agent to form a compound having an imine bond, which is more stable than the hydrazone bond. The reducing agent is, for example, a cyanoborohydride compound.

Figure 2A:
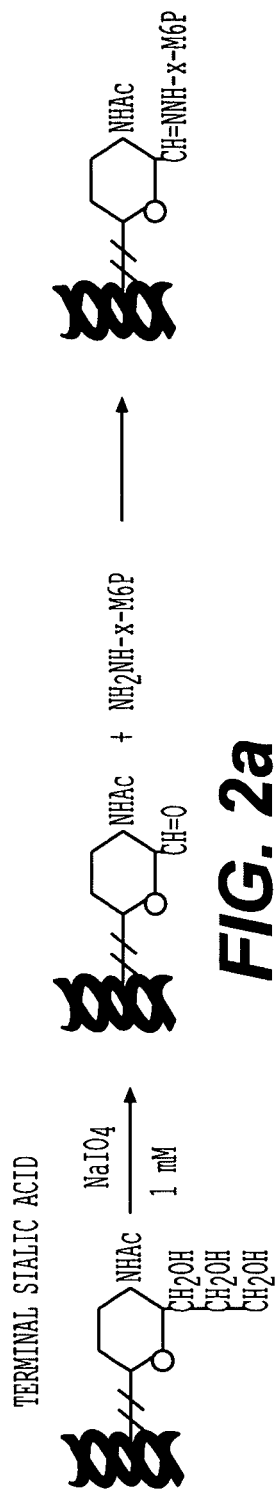
FIGS. 2A-2C are schematic representations of alternative oxidation methods used in the conjugation methods.
Figure 2B:
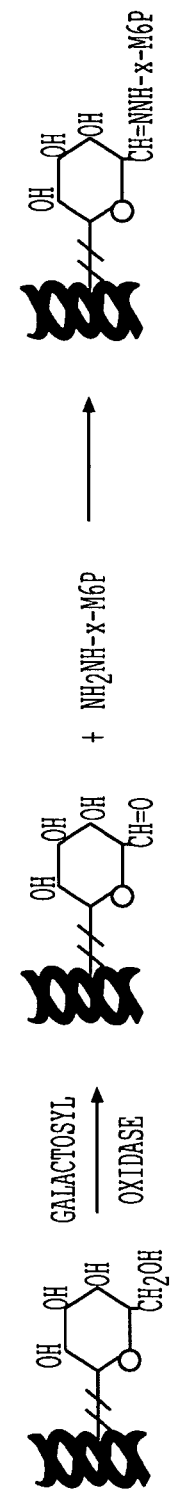
Figure 2C:
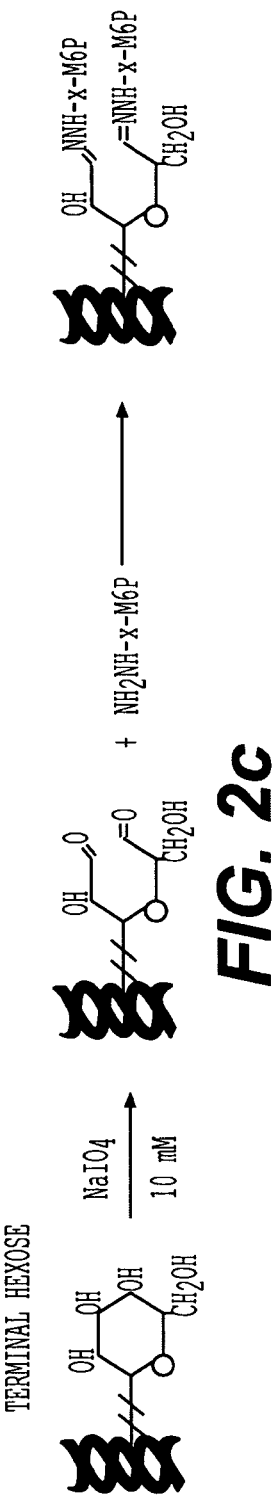

FIG. 1 is a schematic representation of the conjugation methods. In a first step, the reducing terminal sugar of oligosaccharides is derivatized to glycosylhydrazine (as shown) or other carbonyl-reactive groups (such as hydrazide, semicarbozide, aminooxyl, etc). Such oligosaccharides must have one or more phosphate groups attached to the C 6' position(s) on mannopyranosyl groups (M6P). The oligosaccharide derivatives then react with the carbonyl (aldehyde) groups generated in the oxidized carbohydrates on glycoproteins to form covalent bond conjugates. FIGS. 2A-2C depict oxidation of the glycoproteins according to at least three possible methods. By a first method, sialic acids on glycans are oxidized with a low concentration of sodium periodate (less than or equal to 10 mM) to generate the required carbonyl groups. A second method is suitable when terminal galactoses exist on the glycans, in which enzymatic oxidation is used. More specifically, galactose oxidase is used to oxidize the C 6' hydroxyl group on the galactose groups. The second oxidation method should not inactivate the glycoprotein. In an alternative embodiment of the second oxidation method, sialic acid groups on glycoprotein carbohydrates are removed using neuraminidase to expose the terminal galactoses, and then galactose oxidase is used to oxidize the terminal exposed galactoses as described for the first embodiment of the second oxidation method. By a third oxidation method, the hexoses on the glycans are oxidized with relatively high concentrations of sodium periodate, i.e. with sodium periodate having a concentration of greater than about 10 mM and less than about 500 mM, to open the vicinal hydroxyl groups of the sugar ring. This third oxidation method is potentially harmful to certain glycoproteins that are sensitive to oxidation. To protect the glycoproteins from oxidation of amino acids, reductive agents such as beta-mercaptoethanol or cysteine or others are added to the oxidation reaction.

In some of the examples infra, a natural phosphorylated oligosaccharide, the phosphopentamannose derived by mild acid hydrolysis of O-phosphomannan extracted from yeast Hansenula holstii NRRL Y-2448, was used. This compound has a structure of 6-P-M(alpha 1,3)-M(alpha 1,3)-M(alpha 1,3)-M(alpha 1,2)-M (M. E. Slodki, 57 BIOCHIMICA ET BIOPHYSICA ACTA 525 (1962); R. K. Brefthauer et al., 12(7) BIOCHEMISTRY 1251 (1973); L. A. Parolis et al., 309 CARBOHYDR. RES. 77 (1998)). Since the terminal mannosyl in phosphopentamannose is linked to the penultimate mannosyl group via alpha 1,3 linkage, this compound exhibits about 6 fold less affinity towards the MPRs than the alpha 1,2 linked mannosyl oligosaccharides (J. Distler et al., 32(15) J. BIOL. CHEM. 21687 (1991)). Preferred oligosaccharides for therapeutic purposes will be those having the terminal and penultimate mannosyl groups linked via an alpha 1,2 linkage. A trisaccharide bearing a terminal M6P is better than a bisaccharide bearing terminal M6P, and a bisaccharide bearing terminal M6P is better than M6P alone (J. Distler et al., 32(15) J. BIOL. CHEM. 21687 (1991); H. Tomoda et al., 213 CARBOHYDR. RES. 37 (1991)).

While some of the examples are carried out with the natural product of phosphopentamannose derivatized with hydrazine, it will be clear to one skilled in the art that various changes in form and detail can be made without departing from the true scope of the invention. For example, the oligosaccharide compounds useful in the present invention include any oligosaccharides that can be synthesized and derivatized with any chemical group, such as hydrazine, hydrazides, semicarbozide, aminooxyl (L. A. Vilaseca et al., 4(6) BIOCONJUG. CHEM. 515 (1993)) groups, etc., that can react with carbonyl groups. Total synthesis of various mannopyranosyl oligosaccharides containing M6P has been reported (O. P. Srivastava and O. Hindsgaul, 155 CARBOHYDR. RES. 57 (1986); O. P. Srivastava and O. Hindsgaul, 52 J. ORG. CHEM. 2869 (1987); O. P. Srivastava and O. Hindsgaul, 161 CARBOHYDR. RES. 195 (1987)).

In addition, numerous biologically active materials are subject to modification according to the present methods to form novel compounds and compositions. Bioactive materials that are modified by the present methods include glycoproteins, especially lysosomal enzymes isolated from natural sources or produced by recombinant technologies. However, other bioactive materials that are modified by the present methods include antiviral drugs and gene-targeting materials. After modification according to the present methods, the bioactive materials are taken up by target cells through receptor-mediated endocytic pathways. The modified materials do not lose their biological activity, and the covalent bonds are stable at neutral pH between 6.5-7.5 for at least few months in solution at 4° C., or indefinitely if lyophilized (J. Singh Kralovec et al., 29 CANCER IMMUNOL. IMMUNOTHER. 293 (1989)). Once inside the cells, however, the covalent bonds in conjugated materials are cleaved into component oligosaccharide derivatives and the biologically active materials by the low pH in the cellular endosomes and lysosomes (pH<5.5) within a relatively short period of time (G. R. Braslawsky et al., 33 CANCER IMMUNOL. IMMUNOTHER. 367 (1991)).

In another embodiment of this invention, other sugar residues that have cognate carbohydrate-binding receptor are modified according to the present methods, and oligosaccharide chains on a glycoprotein can be extended. For example, mildly oxidized sialic acid can be extended with mannose or galactose to target the mannose receptor or asialoglycoprotein receptor to achieve tissue or cell-specific targeting.

In another application of this invention, anti-viral drugs are modified with M6P to enhance their therapeutic efficacy. During viral infection, viral entry also occurs through receptor-mediated endocytosis. Once in the endosome, the low pH induces fusion of viral membrane with the endosome membrane and releases the viral content to the cytosol to start the replication cycle. Current anti-viral drugs are mostly lipophilic so they can pass through the cell membrane and reach cytosol to be effective; therefore they are general and not cellular compartment specific. M6P modification according to the present methods is especially suitable for developing hydrophilic, cellular compartment-specific anti-viral drugs. Anti-viral drugs with M6P are taken up by the cells through MPR-mediated endocytosis to concentrate in endosomes where virus entry occurs, thus subjecting early stage viral infection to attack by the antiviral compound before viral replication, resulting in improved therapeutic value. A similar approach of involving coupling of AZT to mannosylated BSA, which can be taken up by the mannose-receptor, has been shown to have higher anti-viral activity than the AZT parental drug (G. Molema et al., 34(3) J. MEDICINAL CHEM. 1137 (1991)).

In another embodiment of this invention, the methods are used to modify oligonucleotides useful in gene therapy targeted to correct point mutation in genes. More specifically, the methods are used to modify RNA-DNA chimeric oligonucleotides that are used to repair one or two base pair alterations in the genome of mammalian cells (E. B. Kmiec, 17 ADV. DRUG DELIVERY REVIEWS 333 (1995); K. Yoon et al., 93 PROC. NATL. ACAD. SCI. 2071 (1996)). Such a strategy has been used, for example, to correct the mutation responsible for sickle cell anemia in vitro (A. Cole-Strauss et al., 273 SCIENCE 1386 (1996)), to mutate the rat factor IX gene and UGT in rat liver in vivo (B. T. Kren et al., 4 NATURE MEDICINE 285 (1998); B. T. Kren et al., 96(18) PROC. NATL. ACAD. SCI. 10349 (1999); P. Bandyopadhyay et al., 274 J. BIOL. CHEM. 10163 (2000)) and to correct dystrophin in mdx mouse muscle (T. A. Rando et al., 97(10) PROC. NATL. ACAD. SCI. 5363 (2000)). A critical step for success with this strategy is to deliver the oligonucleotides to target cells with high efficiency. The percentage of gene conversion correlates with the efficiency of oligonucleotide delivery, which is enhanced by modifying polycations or lipsosome with lactose for the asioloalycoprotein receptor on liver hepatocytes (Kren et al. 1998, supra; Kren et al. 1999; supra; Bandyopadhyay et al., supra). In contrast, for the mdx mouse dystrophin, only the muscle near the injection site is converted (Rando et al., supra), presumably because only cells nearby the injection site take up the injected oligonucleotides. Thus, an efficient and general delivery approach of the oligonucleotides for a variety of target cells in vivo is especially useful for expanding the application of such gene therapies. Accordingly, the methods described herein permit M6P modification to provide improved delivery of oligonucleotides to target cells by enhancing MPR-mediated uptake. MPRs are present on a wide variety of cells in vivo and MPR-mediated endocytic process is as efficient an uptake process as the asialoglycoprotein receptor-mediated endocytosis on hepatocytes in liver. PEI/liposome delivery systems employed for the aforementioned oligonucleotides, or the oligonucleotides can be easily modified with M6P or M6P oligosaccharide derivatives, thus to expand the target cell types in vivo for gene-targeted therapy.

The following examples provide illustrative embodiments of the invention. One of ordinary skill in the art will recognize the numerous modifications and variations that may be performed without altering the spirit and scope of the present invention. Such modifications and variations are encompassed within the scope of the invention. The examples do not in any way limit the invention.

EXAMPLES

Example 1

Synthesis of Phosphopentamannose-Hydrazine Derivatives

Phosphopentamannose was prepared from phosphomanan obtained from Dr. M. E. Slodki, Northern Regional Research Laboratory, U.S. department of agriculture, Peoria, Ill. Phosphopentamannose was prepared essentially as described by M. E. Slodki (1962) and has the following structure: 6-P-M (alpha 1,3)-M(alpha 1,3)-M(alpha 1,3)-M(alpha 1,2)-M.

100 mg of lyophilized powder of phosphopentamannose was added into a glass tube, to which 3 ml of anhydrous hydrazine was added. The tube was filled with nitrogen gas, capped with a tight fitting cap, and wrapped with parafilm. The reaction was proceeded at room temperature for 6-18 hours, after which the hydrazine was evaporated under vacuum while the hydrazine was absorbed through a bottle of sulfuric acid. 2 ml of toluene was added and removed by a stream of nitrogen gas to get rid of the residual hydrazine (Tolvanen and Gahmberg, 1986, supra; Gahmberg and Tolvanen, 1994, supra). Phosphopentamannosyl-hydrazine (PPMH) was dissolved in 2 ml of water and dialyzed against 4 liters of 10 mM phosphate buffer (pH 7.0) overnight at 4° C., after which the sample was collected and lyophilized.

Example 2

Coupling of Phosphopentamannose-Hydrazine to Avidin

A. Oxidation of Avidin 1 ml of 2.5 mg/ml of avidin (obtained from Sigma or Pierce) were oxidized with 10 mM sodium periodate in 100 mM sodium acetate (pH 5.6) for 30 minutes at 4° C. in the dark. After which 25 µl of glycerol were added and the sample was incubated on ice for 15 minutes to consume the excess sodium periodate. Samples were then dialyzed overnight against 100 mM sodium acetate (pH 5.6) at 4° C. 0.5 ml of 2.5 mg/ml avidin without periodate oxidation were processed the same way as untreated control. Samples after dialysis were collected and stored at 4 or −20° C. until use.

B. Coupling of phosphopentamannose-hydrazine to oxidized avidin

200 µl of untreated or oxidized avidin (2.5 mg/ml) were mixed with 1 mg of phosphopentamannose-hydrazine dissolved in 20 µl of 100 mM sodium acetate buffer (pH 5.6) and incubated at 37° C. for 1 hour. The samples were dialyzed against 2 liters of CI-MPR binding buffer (50 mM imidazole, 150 mM NaCl, 1 mM EDTA, 0.5 mM $MgCl_2$, 1 mM beta-glycerol phosphate, 0.025% Triton X-100, pH 7.0) overnight at 4° C. Samples were collected after dialysis. 10 µl of untreated avidin/conjugated, oxidized avidin control without conjugation, oxidized avidin/conjugated samples were boiled in SDS sample buffer and separated on 12% SDS-gel to see if there is any mobility shift. 50 µl of the samples are subjected to the CI-MPR binding test. The remaining samples are stored at −20° C. until use.

Figure 3:
FIG. 3 is a SDS-PAGE analysis of different avidins before and after phosphopentamannose-hydrazine conjugation.

FIG. 3 is a SDS-PAGE analysis of different avidins before and after phosphopentamannose-hydrazine conjugation. Lane 1 shows the results for untreated avidin with conjugation. Lane 2 shows the results for oxidized avidin without conjugation. Lane 3 shows the results for oxidized avidin with phosphopentamannose conjugation. Only Lane 3 shows some avidin retardation in migration, indicating conjugation has occurred. As shown in FIG. 3, there is a clear shift of molecular weight in the oxidized avidin/conjugated sample compare to the untreated avidin/conjugated or oxidized avidin without conjugation controls, indicating that the oxidized avidins are coupled to phosphopentamannose-hydrazine. The molecular weight shift is about 1-4 kDa, suggesting 1-4 phosphopentamannose were coupled to one monomer of avidin.

C. Binding of Unconjugated Avidin and Conjugated Avidin to CI-MPR Column

100 µg of untreated avidin/conjugated (unconjugated) and oxidized avidin/conjugated in 0.5 ml CI-MPR binding buffer were passed through a CI-MPR column 5 times, and the final passage was collected as flow-through. The column was washed with 8 volumes of binding buffer, an aliquot of the final wash was collected, and finally the bound avidin were eluted with 0.5 ml of 5 mM M6P in binding buffer. 20 µl of the flow through, the final wash and the eluted samples were separated on SDS-gel as described for FIG. 3.

Figure 4:
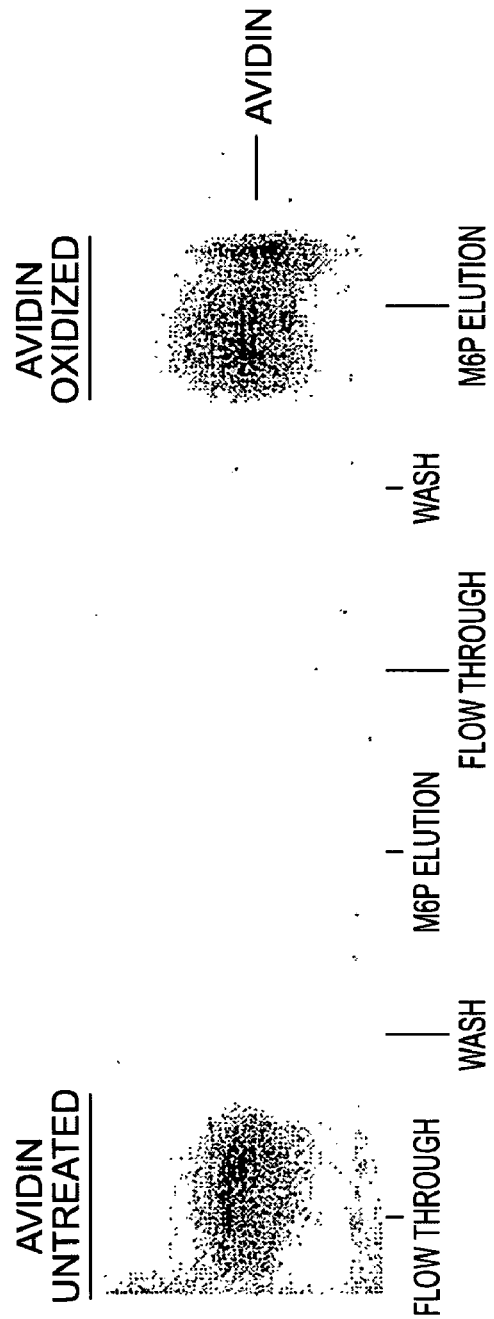
FIG. 4 is a CI-MPR binding analysis of untreated avidin and oxidized avidin conjugated with phosphopentamannose-hydrazine.

FIG. 4 is a CI-MPR binding analysis of untreated avidin and oxidized avidin conjugated with phosphopentamannose-hydrazine. As is shown in FIG. 4, none of the untreated/conjugated avidin binds to the CI-MPR column, whereas all the oxidized avidin/conjugated binds to the CI-MPR column, indicating the efficiency of coupling of phosphopentamannose-hydrazine to oxidized avidin is nearly 100%. The oxidized avidin/unconjugated sample, as the untreated avidin, also does not bind to CI-MPR column (data not shown), indicating the coupling procedure is specific.

Example 3

Conjugation of Phosphopentamannose-Hydrazine to Beta-Glucuronidase Does Not Inactivate the Enzyme One major concern about the conjugation is that lysosomal enzymes conjugated in such a way must retain enzymatic activity, preferably full activity. While the avidin conjugation result clearly has shown that the coupling process is highly efficient, whether the coupling process affect its biological activity is unknown, in particular, avidin is a stable protein, not an enzyme. Therefore in the following example, lysosomal enzyme beta-glucuronidase isolated from bovine liver (50,000 U/mg, not completely pure, purchased from Sigma) was used.

A. Oxidation 6 mg of beta-glucuronidase were dissolved in 1.5 ml of water, 1.3 ml of the material (4 mg/ml) were dialyzed against 100 mM NaAc (pH 5.6) overnight at 4° C. 200 µl of the rest of the sample were kept at 4° C. as water-control.

Of the sodium acetate dialyzed beta-glucuronidase, 0.5 ml were kept as untreated-dialyzed material, 0.8 ml were oxidized with 10 mM sodium periodate at 4° C. for 30 minutes. After which 20 µl glycerol were added and the sample mixed on ice for 10 minutes to decompose all the excess sodium periodate, then the oxidized material was dialyzed against 1 liter 100 mM sodium acetate overnight. 0.4 ml of the sample was kept at 4° C. as oxidized-dialyzed control. The other 0.5 ml of sample were used for phosphopentamannose-hydrazine coupling.

B. Coupling 3 mg of phosphopentamannose-hydrazine were dissolved in 25 µl of 100 mM NaAc (pH, 5.6) and mixed with 0.5 ml oxidized beta-glucuronidase (4 mg/ml) and incubated at 37° C. for 2 hours, the coupled sample was dialyzed against CI-MPR binding buffer overnight.

C. Enzymatic Activity of Variously Treated Beta-Glucuronidase

To 200 µl of 100 mM p-nitrophenyl beta-glucuronide in 100 mM sodium acetate (pH 5.0), 15 µl of water as negative control, 15 µl of beta-glucuronidase dissolved in water, 15 µl of sodium acetate dialyzed-untreated beta-glucuronidase, 15 µl of oxidized-dialyzed beta-glucuronidase and 15 µl of oxidized beta-glucuronidase+phosphopentamannose-hydrazine were added. After incubation at 37° C. for 1 hr, 200 µl of 200 mM glycine (pH 10.4) were added. OD of each sample was measured at 400 nm.

The results of one such experiment are described in Table 1.

TABLE 1

| Sample | OD at 400 nM |
|---|---|
| 15 µl water | 0.00 |
| 15 µl beta-glucuronidase dissolved in water | 1.40 |
| 15 µl untreated NaAc dialyzed beta-glucuronidase | 1.37 |
| 15 µl oxidized beta-glucuronidase NaAc-dialyzed | 1.43 |
| 15 µl oxidized beta-glucuronidase plus phosphopentamannose | 1.44 |

Figure 5:
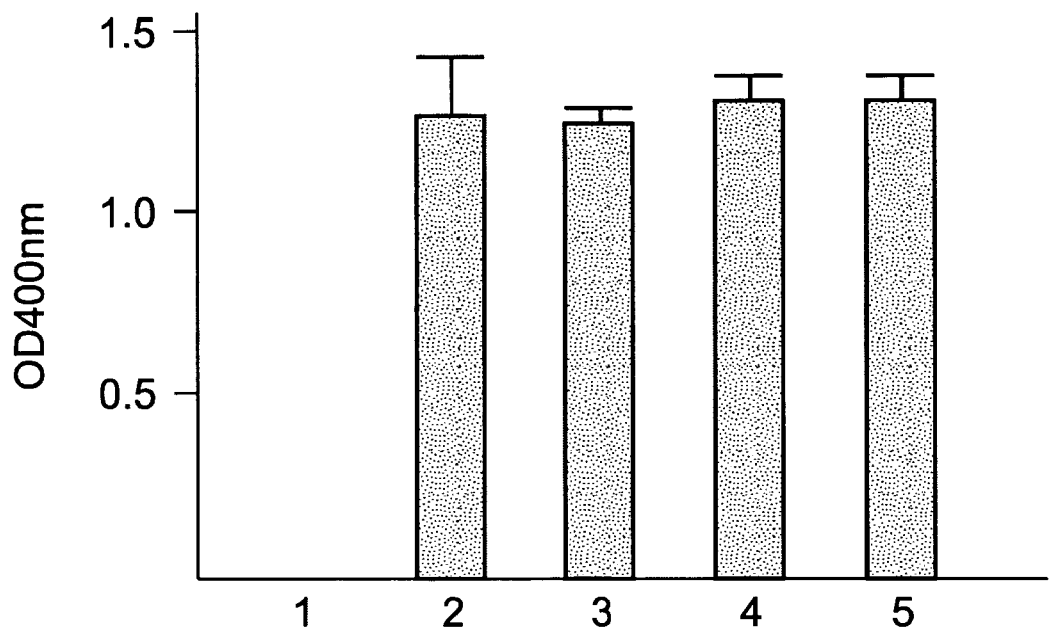
FIG. 5 is a bar graph showing enzymatic activity of beta-glucuronidase after different treatments including after conjugation.

FIG. 5 is a bar graph showing enzymatic activity of beta-glucuronidase after different treatments including after conjugation. 1 is $H_2O$ control; 2, beta-glucuronidase dissolved in $H_2O$; 3, beta-glucuronidase dialyzed against NaAc (pH 5.6); 4, oxidized beta-glucuronidase dialyzed against NaAc, and 5, oxidized beta-glucuronidase conjugated with phosphopentamannose-hydrazine. The results represent an average of three experiments and indicate nearly equal beta-glucuronidase activity in all samples. Thus, the overall procedure did not appear to inactivate the beta-glucuronidase. This result is expected because the coupling procedure does not involve the protein backbone, and thus should not affect the overall protein conformation.

D. CI-MPR Binding and Beta-Glucuronidase Assay

100 µl of untreated beta-glucuronidase (CI-MPR binding buffer dialyzed) and 100 µl of oxidized beta-glucuronidase+phosphopentamannose-hydrazine conjugated (CI-MPR binding buffer dialyzed) were mixed with 400 µl of CI-MPR binding buffer (pH 7.0). 50 µl of each sample were saved as starting material for late beta-glucuronidase assay.

450 µl of each sample were passed over a 2 ml CI-MPR column (pre-equilibrated with CI-MPR binding buffer) 5 times. The flow-through of each sample was saved. The column was washed with 8 volumes of CI-MPR binding buffer, the last 0.5 ml was saved as final wash. Finally, the column was eluted with 5 mM M6P in CI-MPR binding buffer by passing over the column 4 times, the eluates were collected as M6P elutions. Therefore each sample has 3 fractions plus the starting material controls. The beta-glucuronidase assay is described below.

To 200 µl of 100 mM p-nitrophenyl glucuronide in 100 mM sodium acetate buffer (pH 5.0), 30 µl of water, 30 µl of untreated beta-glucuronidase column starting material, 30 µl of untreated beta-glucuronidase flow-through, 30 µl of untreated beta-glucuronidase wash, 30 µl of untreated beta-glucuronidase M6P elution, 30 µl of oxidized beta-glucuronidase+PPMH (imidazole) column starting material, 30 µl of untreated beta-glucuronidase+PPMH flow-through, 30 µl of untreated beta-glucuronidase+PPMH wash, 30 µl of untreated beta-glucuronidase+PPMH M6P elution, were added, the samples were incubated at 37° C. for 1 hour. 200 µl of 200 mM glycine (pH 10.4) was added to each sample to stop the reaction and OD400 nm was measured.

The results from one such experiment are summarized in Table 2.

TABLE 2

| Sample | O.D. at 400 nm |
| --- | --- |
| 30 µl water | 0.00 |
| 30 µl untreated beta-glucuronidase column starting material | 1.43 |
| 30 µl untreated beta-glucuronidase flow-through | 1.36 |
| 30 µl untreated beta-glucuronidase wash | 0.00 |
| 30 µl untreated beta-glucuronidase M6P elution | 0.00 |
| 30 µl untreated beta-glucuronidase + PPMH column starting material | 1.41 |
| 30 µl untreated beta-glucuronidase + PPMH flow-through | 0.27 |
| 30 µl untreated beta-glucuronidase + PPMH wash | 0.00 |
| 30 µl untreated beta-glucuronidase + PPMH M6P elution | 0.06 |

Figure 6:
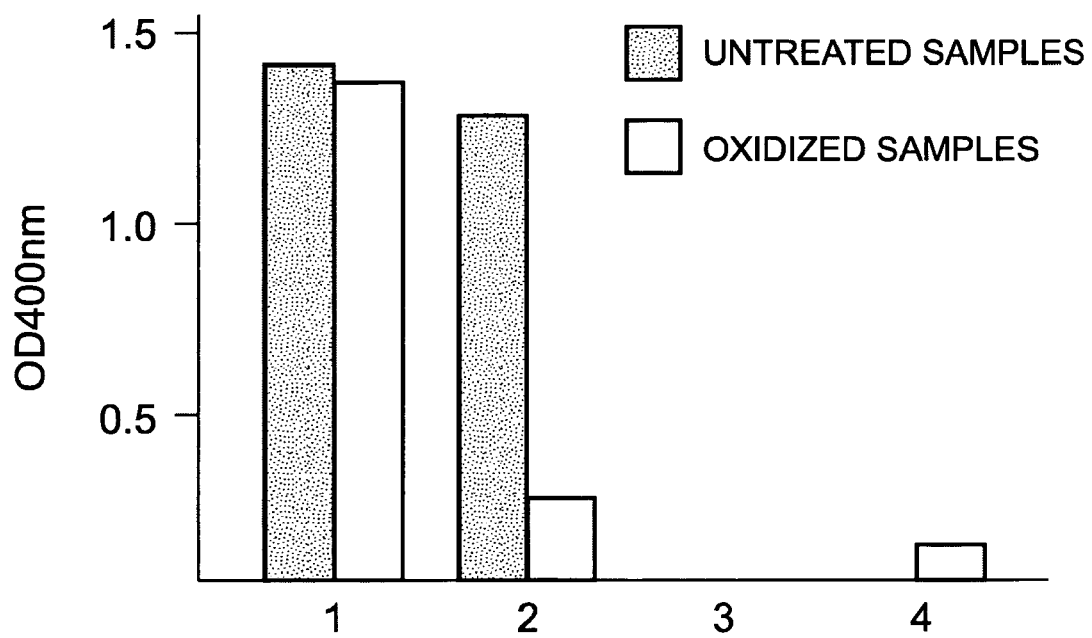
FIG. 6 is a bar graph comparing CI-MPR binding of untreated and oxidized phosphopentamannose-conjugated beta-glucuronidase.

FIG. 6 is a bar graph comparing the CI-MPR binding results for untreated and oxidized phosphopentamannose-conjugated beta-glucuronidase. For the untreated material, nearly 100% of the starting activity was in the flow through, nothing was in the final 0.5 ml wash and M6P elution fractions. However, for the oxidized beta-glucuronidase+ phosphopentamannose-hydrazine sample, only 19% of the starting activity was in the flow through, nothing in the final 0.5 ml wash and about 5% was in the M6P elution fraction.

For the untreated sample, the total beta-glucuronidase activities in the starting material and in the flow-through are about equal so there is no clear loss of sample during the column binding. However, for the oxidized/conjugated beta-glucuronidase sample, the total activity of the flow-through and the M6P elution does not add up to the total activity of the starting material. This is not due to the loss of enzymatic activity by oxidation (FIG. 5), but due to the fact that the oxidized beta-glucuronidase conjugated to phosphopentamannose has relatively low binding affinity to CI-MPR (J. Distler et al., supra), especially when one oxidized glycan was conjugated to only one phosphopentamannose-hydrazine due to steric hindrance of the vicinal aldehyde groups. The binding of oligomannosyl phosphate substrates to CI-MPR column has been well characterized (P. Y. Tong et al., 264(14) J. BIOL. CHEM. 1962 (1989); J. Distler et al., supra). The monophosphate form of oligomannosyl substrate binds to CI-MPR column with low-affinity compare to the bisphosphorylated substrate, with large portion of the monophosphate substrate being eluted during the washing step and the rest eluted with M6P, whereas the bisphosphorylated substrate can only be eluted with M6P (P. Y. Tong et al., supra). Therefore, the most likely possibility is that the oxidized beta-glucuronidase conjugated with phosphopentamannose-hydrazine may just behave like the substrate with only one monophosphate and being lost in the first few volumes of washing buffer.

Example 4

Preparation of Modified Recombinant Human Acid α-glucosidase (neo-rhGAA)

A. Endoglycosidase H Digestion of α-galactosidase A

One gram of purified recombinant human α-galactosidase A (Genzyme Corp., Cambridge, Mass.) was reconstituted in 180 ml of deionized water and dialyzed twice against 4 liters of 25 mM acetate buffer (pH 5.6) for 18 hours. The dialyzed α-galactosidase A was subsequently mixed with 20 ml of 0.5 M citrate buffer (pH 5.5) containing 1% β-mercaptoethanol. Digestion was performed with 50,000 units of endoglycosidase Hf (New England Biolabs, Beverly, Mass.) at 37° C. for 4 hours or until completion, as determined by SDS-PAGE. Following digestion, the sample was filtered through a Centriprep-20 column with a molecular weight cut off of 5000 Da (Millipore, Bedford, Mass.). The filtrate containing the released oligosaccharide was collected and dialyzed against three changes of 4 liters of deionized water at 4° C.

B. Isolation and Derivatization of M6P-containing Oligosaccharide

M6P-containing oligosaccharides were released from recombinant α-galactosidase A (Genzyme Corp) by digesting with endoglycosidase Hf (New England Biolabs) and purified according to the method of Varki and Kornfeld (255 J. BIOL. CHEM. 10847-10858 (1980)) with minor modifications. The dialyzed oligosaccharides were adjusted to 2 mM Tris and then loaded onto a 20 ml QAE-sephadex A column that had been equilibrated with the same buffer at a flow rate of 1.5 ml/min. The column was washed sequentially with 2 mM Tris containing 20 mM and 70 mM NaCl, and the M6P-containing oligosaccharides were eluted with 2 mM Tris containing 200 mM NaCl. The purified M6P-containing oligosaccharides and the phosphopentamannose were derivatized to glycosylhydrazines using the method of Tolvanen and Gahmberg. (261 J. BIOL. CHEM. 9546-9551 (1986)).

C. Chemical Conjugation of Derivatized M6P-Containing Oligosaccharides onto rhGAA Recombinant human acid α-glucosidase (rhGAA) was dialyzed twice against 2 liters of 0.1 M sodium acetate (pH 5.6) for 18 hours at 4° C. The nucleotide sequence of rhGAA is shown in SEQ ID NO:1 and the amino acid sequence of rhGAA is shown in SEQ ID NO:2. The dialyzed rhGAA (5 mg/ml) was oxidized with 2 mM sodium meta-periodate for 30 minutes on ice. Excess sodium meta-periodate was removed by the addition of 0.5 ml of 50% glycerol and incubation on ice for 15 minutes. The oxidized enzyme was then dialyzed against 2 liters of 0.1 M sodium acetate (pH 5.6). Fifty mg aliquots of the oxidized rhGAA were conjugated to 10 mg of hydrazine-derivatized M6P-containing oligosaccharides or 20 mg of phosphopentamannose by mixing and incubating at 37° C. for 2 hours. After conjugation, both the M6P- and phosphopentamannose-conjugated rhGAA samples were dialyzed against 4 liters of 25 mM sodium phosphate buffer (pH 6.75) containing 1% mannitol and 0.005% Tween-80 for 18 hours at 4° C. and then sterile filtered. The samples were aliquoted, snap-frozen on dry ice and stored at −80° C. until further analysis.

Example 5

Process for Chemically Conjugating M6P-Containing Oligosaccharides onto rhGAA Did Not Affect its Enzymatic Activity Direct chemical conjugation of oligosaccharides onto a protein backbone via reductive amidation or maleimide chemistries frequently requires prolonged incubations at neutral to alkaline pH. These reaction conditions are destabilizing to lysosomal enzymes such as GAA that have optimal activities at acidic pH. In order to minimize the inactivation of GAA, a conjugation method was used which employed a condensation reaction between an aldehyde group and a hydrazine to form a hydrozone bond. In this method, M6P-containing oligosaccharides were derivatized to glycosylhydrazines and then conjugated (at acidic pH) to rhGAA, the sialic acids of which had been oxidized with periodate to aldehydes. Conjugating the M6P-containing moieties directly onto the existing oligosaccharide side chains of rhGAA also confers spacer length that could minimize the effect of steric hindrance during receptor binding.

Figure 7:
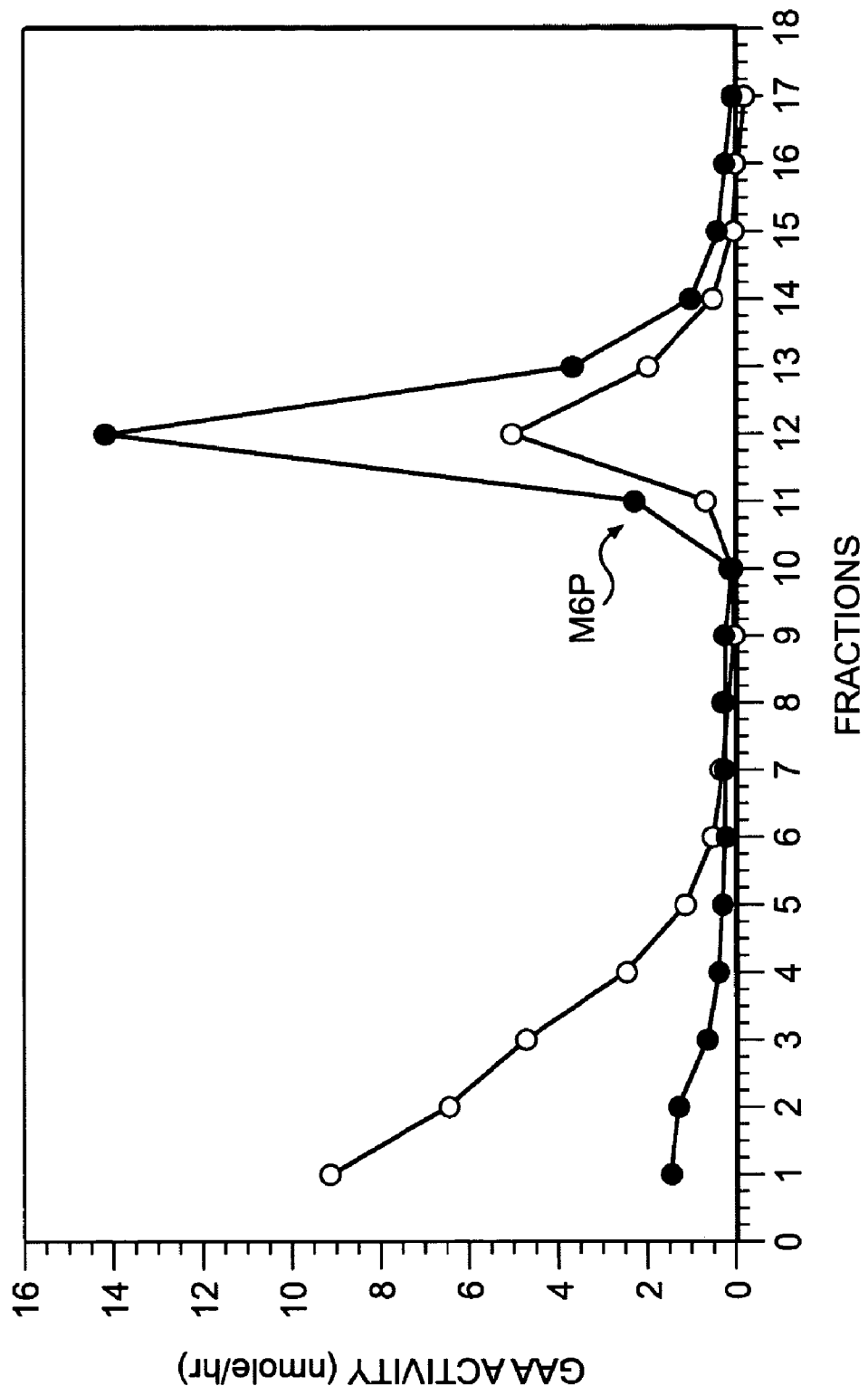
FIG. 7 depicts GAA activity, measured in nmole/hour, in fractions obtained from a CI-MPR column following binding of recombinant human GAA (shown by open circles), and phosphopentamannose-conjugated rhGAA (shown by closed circles) to the CI-MPR column.

Additionally, conjugation of phosphopentamannose-hydrazine onto rhGAA did not affect the enzyme's hydrolytic activity (data not shown). Conjugation efficiency was determined to be high and to have occurred on nearly all the rhGAA molecules, as evidenced by an increase in the binding of the phosphopentamannose-conjugated rhGAA to a CI-MPR column, shown in FIG. 7, where closed circles represent conjugated rhGAA and open circles represent rhGAA. While only approximately 40% of the original rhGAA bound the CI-MPR column, the column retained greater than 90% of the phosphopentamannose-conjugated rhGAA. Therefore, the conjugation process used to modify the oligosaccharides on rhGAA was efficient and did not measurably alter its activity. However, conjugation with phosphopentamannose did not enhance its uptake into L6 myoblasts in vitro when compared to the unmodified enzyme (data not shown). This may be attributed to relatively low-affinity of phosphopentamannose to CI-MPR.

Example 6

Conjugation of Mono- and Bis-Phosphorylated Oligomannose Residues onto Rhgaa Improved its Binding to CI-Mpr Soluble CI-MPR was purified from fetal bovine serum using a phosphopentamannose column according to the method of Li et al. (1 GLYCOBIOLOGY 511-517 (1991)). The purified CI-MPR (1 mg) was coupled to 1 ml Affigel-15 beads (BioRad) essentially as outlined by the manufacturer. Binding of rhGAA or M6P-conjugated rhGAA to the CI-MPR column was performed as described by Valenzano et al. (270 J. BIOL. CHEM. 16441-16448 (1.995)). The M6P content of rhGAA and modified rhGAA (neo-rhGAA) was analyzed using the method described by Zhou et al. (306 ANAL. BIOCHEM. 163-170 (2002)). Oligosaccharide profiling of the purified M6P-containing oligosaccharides following endoglycosidase Hf digestion of α-galactosidase A was performed according to the method of Townsend and Hardy. (1 GLYCOBIOLOGY 139-147 (1991)).

Figure 8A:
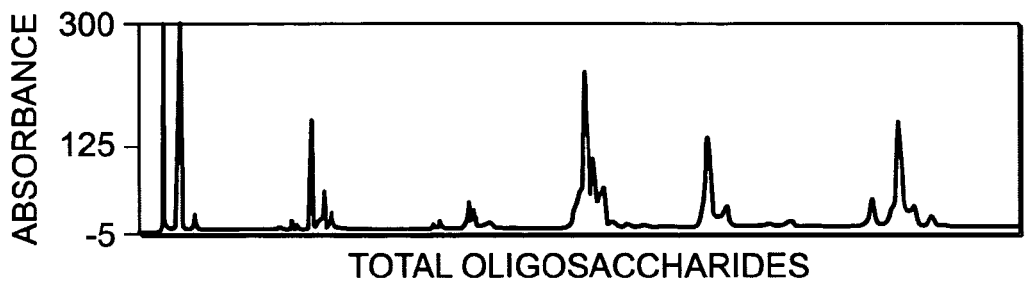
FIG. 8A depicts the results of a chromatographic analysis of oligosaccharides released following digestion of α-galactosidase A with endoglycosidase H.
Figure 8B:
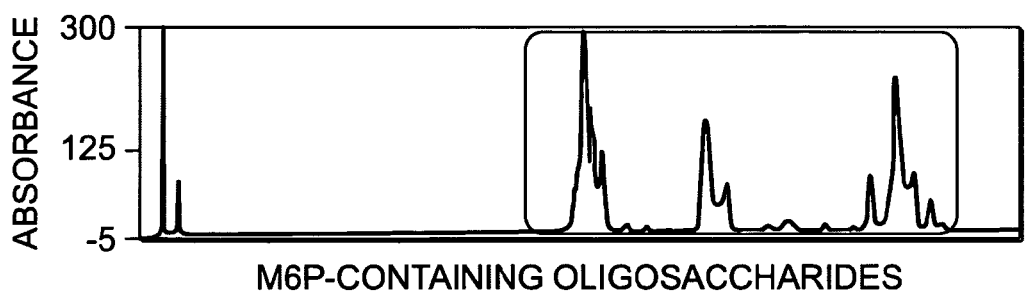
FIG. 8B depicts the results of a chromatographic analysis of oligosaccharides following purification of the M6P-containing fraction over a QAE column by dionex column chromatography.

To generate a modified rhGAA (neo-rhGAA) with high affinity for the CI-MPR, M6P-containing oligosaccharides were isolated from recombinant human α-galactosidase A and conjugated onto rhGAA, as described supra. Recombinant α-galactosidase A was used as a source of the oligosaccharides because analysis of its carbohydrate content, as shown in FIG. 8A, indicated that 30 to 40% of the high-mannose oligosaccharides are bis-phosphorylated in α-galactosidase A, which is expected to result in high affinity for the CI-MPR. Phosphorylated high mannose oligosaccharides (both mono- and bis-phosphorylated) were released from α-galactosidase A by endoglycosidase H treatment, purified over a QAE column and analyzed by dionex column chromatography, shown in FIG. 8B.

Figure 9:
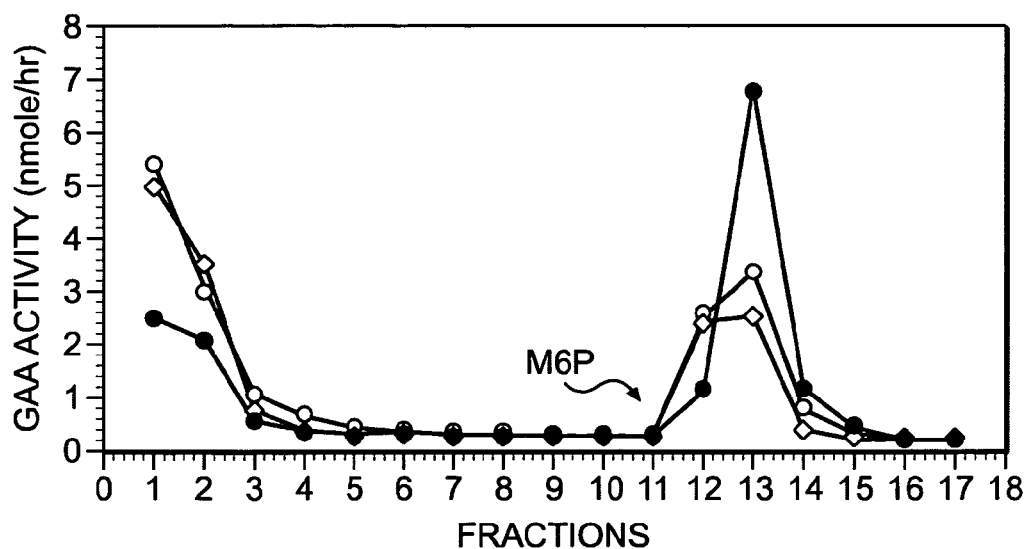
FIG. 9 depicts GAA activity in fractions obtained following binding of rhGAA (shown by open circles), modified rhGAA (neo-rhGAA) (shown by closed circles) and periodate-treated rhGAA (shown by open squares) to a CI-MPR column.

Conjugation of the purified mono- and bis-phosphorylated oligosaccharides onto rhGAA (neo-rhGAA) resulted in an increase in the fraction of enzyme that bound to the CI-MPR column, as shown in FIG. 9, which shows an increase in binding of neo-rhGAA to the CI-MPR column (represented by closed circles), relative to rhGAA (represented by open circles), and periodate-treated rhGAA (represented by open squares).

As depicted in FIG. 9, approximately 63% of the modified rhGAA (neo-rhGAA) bound to the CI-MPR column compared to approximately 40% for the unmodified enzyme. The periodate-treated non-conjugated rhGAA (open squares in FIG. 9) displayed binding characteristics that were similar to that for untreated rhGAA, (open circles in FIG. 9), suggesting that the increased binding of neo-rhGAA (closed circles in FIG. 9) was not-due to non-specific interactions between the oxidized sialic acids on rhGAA and the CI-MPR column.

A likely reason for a lower than expected fraction of rhGAA containing mono- and bis-M6P (63%, as opposed to $\geq$90% for phosphopentamannose-conjugated rhGAA) to bind the CI-MPR column is that smaller amounts of the phosphorylated oligosaccharides were used in the conjugation reaction.

Example 7

Conjugation of Mono- and Bis-Phosphorylated Oligomannose Residues onto rhGAA Improved its Uptake into Cells In Vitro L6 myoblast cells (ATCC) were plated onto 12-well culture dishes and allowed to settle for 24 hours. Prior to the addition of enzyme to the cells, cells were washed once with 3 ml DMEM (Invitrogen, Carlsbad, Calif.). Various forms of rhGAAs in 1 ml of uptake media (DMEM containing 1% (v/v) heat inactivated FBS, 25 mM Hepes (pH 6.8), 2.5 mM β-glycerolphosphate and antibiotics) were added to cells and incubated at 37° C. for 18 hours. In some of the wells, 5 mM M6P was added to inhibit CI-MPR mediated uptake. After 18 hours, cells were washed twice with PBS containing 1 mM M6P and then twice more with PBS alone. Cells were lysed in GAA assay buffer (0.2 M sodium acetate, 0.4 M potassium chloride, pH 4.3) containing 0.1% Triton X-100 by scraping the cells followed by sonication. Cell lysates were centrifuged at 14,000 g for 10 min at 4° C. and the GM activity in the cleared supernatants was assayed using the fluorogenic substrate 4-methylumbelliferyl-α-D-glucopyranoside. (Sigma Chemical Co., St. Louis, Mo.) (J. L. Van Hove et al., 9 PROC. NATL. SCI. USA 65-70 (1996)). Protein content in the cell lysates was determined using the microBCA kit (Pierce) with BSA as a standard.

Figure 10:
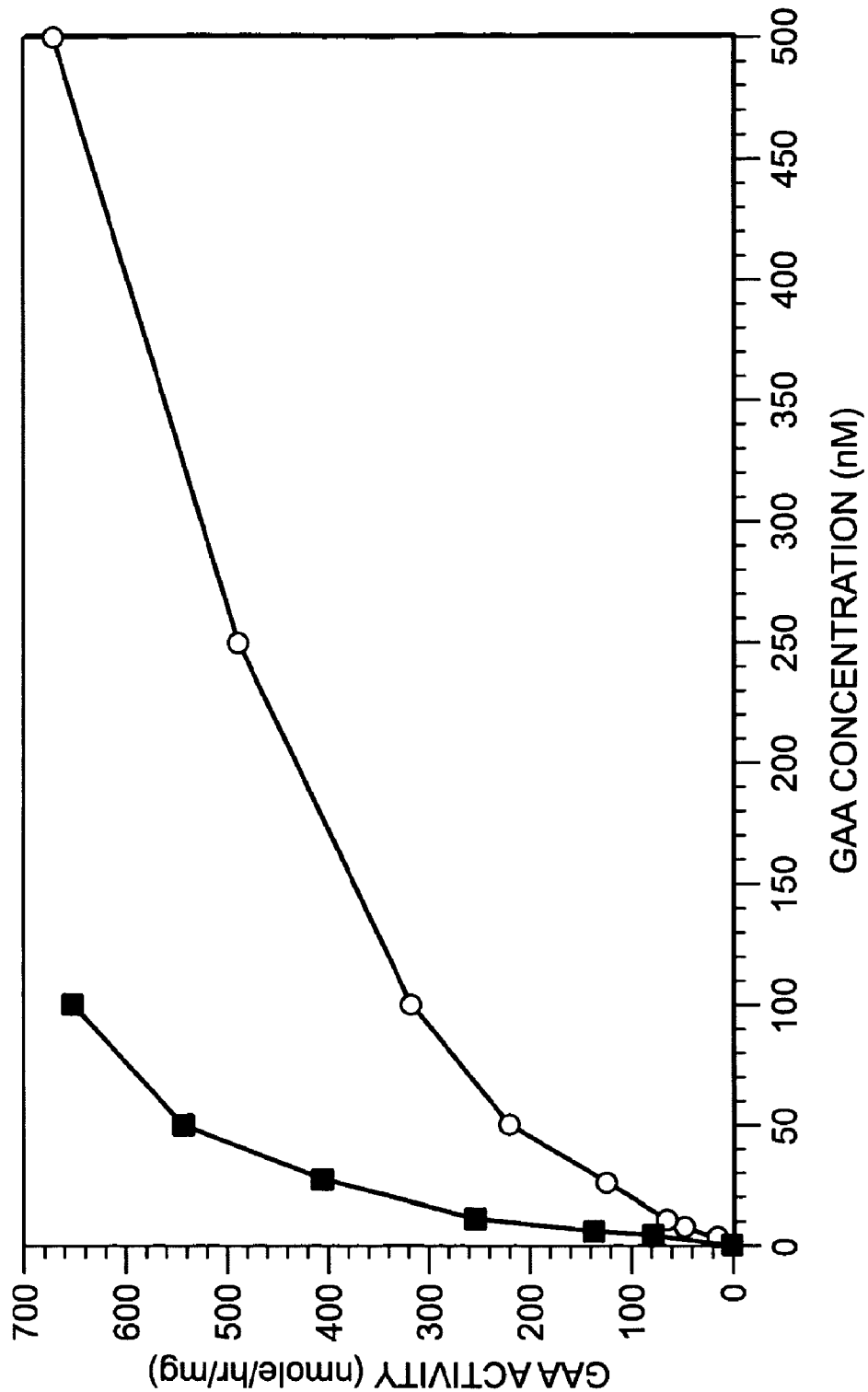
FIG. 10 depicts a graph showing the in vitro uptake of the modified rhGAA (neo-rhGAA) into L6 myoblasts. Open circles represent increasing amounts of rhGAA and closed squares represent increasing amounts of modified rhGAA (neo-rhGAA). Endogenous GAA levels were subtracted from the data presented.

Monosaccharide analysis of the neo-rhGAA confirmed that the modified enzyme contained higher levels of phosphorylated oligomannose residues. The M6P content was increased from about 0.9 mole M6P/mole of unmodified rhGAA, to 2.9 mole M6P/mole of modified rhGAA (neo-rhGAA). Importantly, this increase in M6P-containing oligosaccharides on neo-rhGAA resulted in a significant enhancement in its uptake by L6 myoblasts, as shown in FIG. 10. GM activity was measured for increasing amounts of rhGAA (open circles in FIG. 10) or neo-rhGAA (closed squares in FIG. 10). Uptake of neo-rhGAA approached saturation at 100 nM compared to approximately 500 nM for the unmodified rhGAA. This is consistent with an increase in the affinity of neo-rhGAA for the CI-MPR, presumably because of the conjugation of additional M6P-containing ligands. Uptake was completely blocked by the addition of excess M6P, confirming that the uptake of the enzyme by the L6 cells was primarily mediated via the CI-MPR (data not shown).

Example 8

Clearance of Glycogen from Pompe Mouse Tissues was Improved With Neo-rhGAA

In order to determine whether the improved uptake of modified rhGAA (neo-rhGAA) in vitro in cells correlates with a greater reduction in glycogen storage in vivo in mice, Pompe mice were treated either with neo-rhGAA or unmodified rhGAA. (N. Raben et al. 273 J. BIOL. CHEM. 19086-19092 (1998)). Animal experiments were conducted in accordance with the Guide for the Care and Use of Laboratory Animals (U.S. Department of Health and Human Services, NIH Publication No 86-23).

Four to five month-old Pompe mice were used to evaluate the relative ability of various rhGAAs to reduce glycogen storage in the affected tissues. (N. Raben et al. supra). Groups of Pompe mice (7 animals/group) were injected via the tail vein with a vehicle (25 nM sodium phosphate, pH 6.5; 1% mannitol; 0.005% Tween-80) and varying doses of rhGAA or modified rhGAA (neo-rhGAA). Mice were administered three weekly doses and killed two weeks after the last treatment. Various tissues including the heart, diaphragm and skeletal muscles were collected and stored at −80° C. until further analysis. Statistical analysis was performed using one-way ANOVA followed by a Newman-Keuls test. A probability value of $P<0.05$ was considered statistically significant.

The glycogen content in the various muscles of the Pompe mice was assayed by measuring the difference in the amount of glucose released from a boiled tissue homogenate following digestion in presence or absence of *Aspergillus niger* amyloglucosidase, as described previously. (A. Amalfitno et al., 96 PROC. NATL. ACAD. SCI. USA 8861-8866 (1999)). The glucose levels were assayed using the Amplex Red glucose assay kit (Molecular Probes, Eugene, Oreg.), according to the manufacturer's instructions. Bovine liver glycogen (Sigma Chemical Co.) was used as a standard. In some studies, glycogen content was measured using periodic acid Schiff (PAS) staining followed by computer-assisted histomorphometric analysis (Metamorph) as described previously. (N. Raben et al., 80 MOL. GENET. METAB. 159-169 (2003)). All photography and MetaMorph analyses were performed in a blinded manner.

Approximately 24% and 46% higher enzyme levels were detected in the skeletal muscle and heart tissues, respectively, in animals that were administered neo-rhGAA compared to those treated with the unmodified rhGAA. Treatment with either form of the enzyme (modified neo-rhGAA or unmodified rhGAA) resulted in a dose-dependent reduction in the glycogen levels in all tissues examined, as depicted in FIGS. 11A-11D, which is representative of two independent experiments with 7 animals in each group. However, mice treated with neo-rhGAA uniformly displayed a greater reduction in levels of glycogen in all the muscles analyzed, as depicted in FIGS. 11A-11D.

Figure 11B:
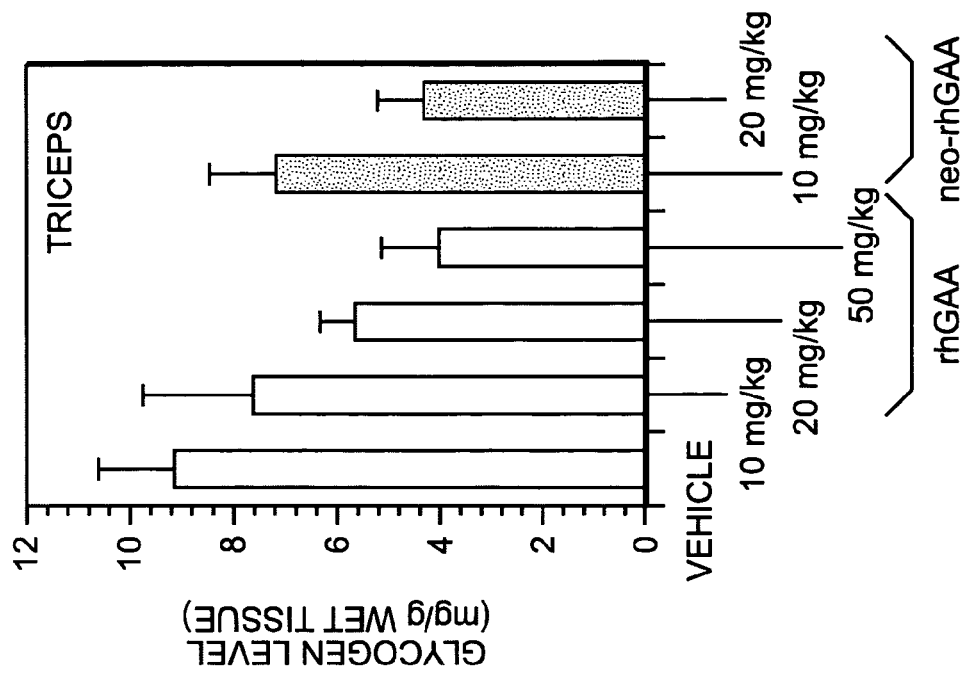
FIGS. 11A-11D depict graphs representing the level of glycogen in heart (11C), skeletal muscles (Quadriceps in 11A; Triceps in 11B), and diaphragm (11D) of Pompe mice treated with varying doses of either rhGAA or neo-rhGAA.
Figure 11A:
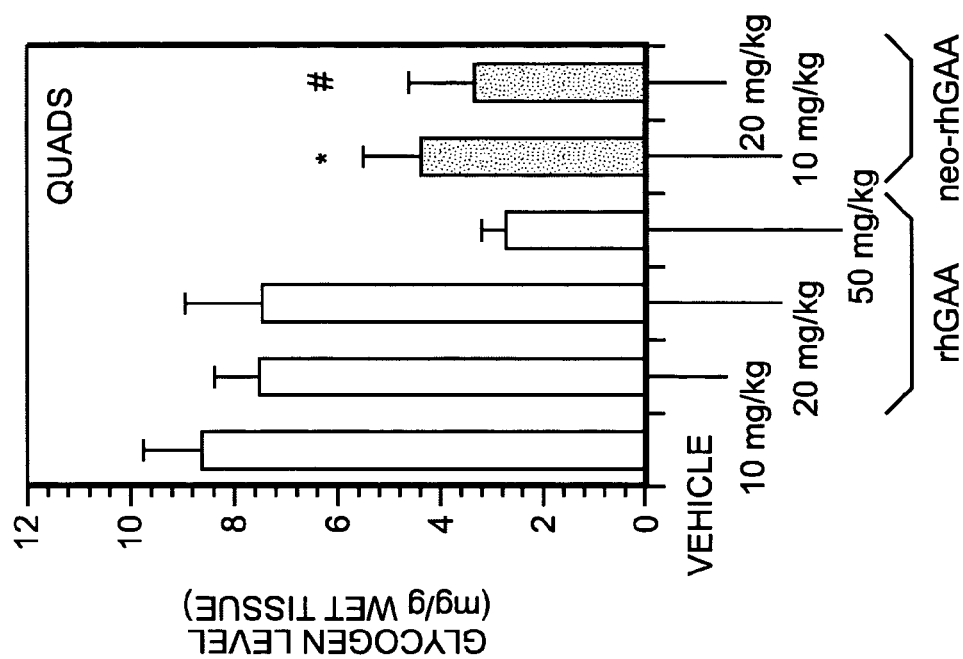
Figure 11C:
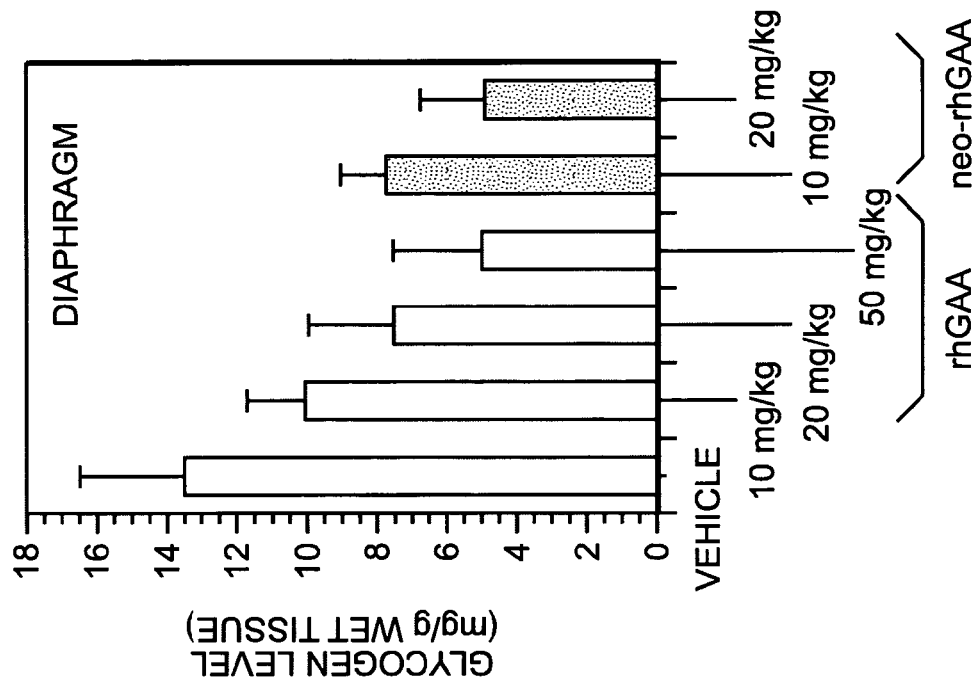
Figure 11D:
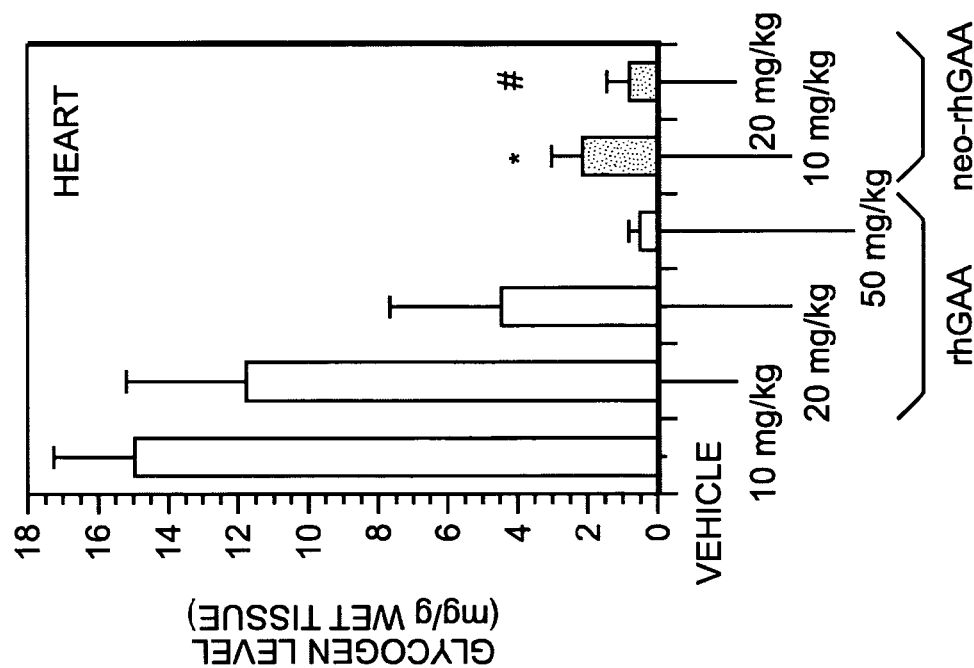

In the heart, an approximately four to six fold greater reduction in glycogen levels was attained with neo-rhGAA than with rhGAA at both the 10 and 20 mg/kg doses (FIG. 11C). Significantly higher reduction in glycogen levels was also observed in the other muscle tissues of animals that had been treated with the modified enzyme, as summarized in FIGS. 11A, 11B and 11D. An approximately 50% reduction in glycogen level was attained with 20 mg/kg neo-rhGAA in the quadriceps muscle (FIG. 11A) and to a lesser degree in the triceps (FIG. 11B) and diaphragm (FIG. 11D). In nearly all cases, the efficacy attained with only 20 mg/kg of modified rhGAA (neo-rhGAA) was similar to that achieved with 50 mg/kg of unmodified rhGAA, thereby suggesting that a lower dose of the modified rhGAA was sufficient to attain a desirable result. In general, the skeletal muscle tissue was more refractory than the heart and attained only a 50-60% reduction in glycogen levels at the 20 mg/kg dose compared to a nearly a 95% reduction in glycogen levels in the heart. (N. Raben et al., 80 MOL. GENET. METAB. 159-169 (2003); N. Raben et al., 6 MOL. THER. 601-608 (2002)).

Figure 12:
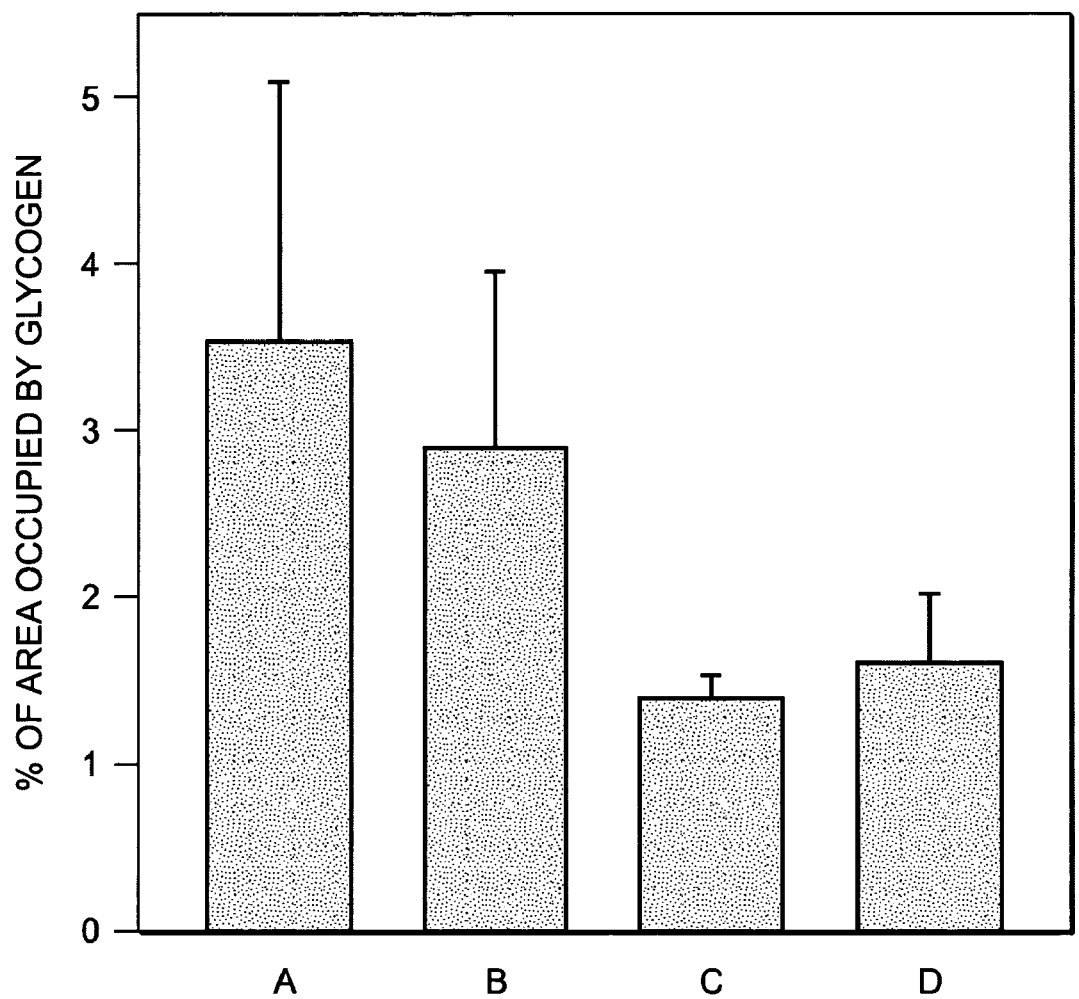
FIG. 12 depicts a bar graph showing the percentage of area occupied by glycogen in quadriceps muscle of Pompe mice treated with vehicle control (A); 10 mg/kg rhGAA (B); 50 mg/kg rhGAA (C); and 20 mg/kg neo-rhGAA (D).

The reduction in glycogen levels observed by biochemical analysis was confirmed by histomorphometric assessment of the quadriceps muscles obtained from the same animals. Tissue samples were stained for lysosomal glycogen followed by analysis of tissues by high resolution light microscopy (HRLM). Lysosomal glycogen appeared as discreet, purple beaded structures scattered throughout each myocyte (data not shown). With enzyme treatment, however, these glycogen-containing structures became smaller and fewer in number. The administration of 20 mg/kg of modified rhGAA (neo-rhGAA) resulted in about a 54% reduction in the tissue area occupied by glycogen, when compared to the vehicle treated negative control samples. This reduction was nearly as effective as the administration of 50 mg/kg of unmodified rhGAA which provided for nearly a 60% reduction, suggesting that neo-rhGAA was 2 to 2.5 times more potent than rhGAA. The results from one such experiment are summarized in FIG. 12, which depicts the percentage of area occupied by glycogen in quadriceps muscle sample in vehicle control (A); 10 mg/kg rhGAA (B); 50 mg/kg rhGAA (C); and 20 mg/kg neo-rhGAA (D).

Example 9

Modifying rhGAA with Synthetic Bis-M6P Glycans Increased its Binding to CI-MPR Without Affecting its Enzymatic Activity A. Derivation of Synthetic bis-M6P-Oligomannose Hydrazide In order to determine whether synthetic forms of modified rhGAA would be as or more effective than the neo-rhGAA described above, synthetic bis-M6P oligomannose oligosaccharides were conjugated onto rhGAA.

Figure 13A:
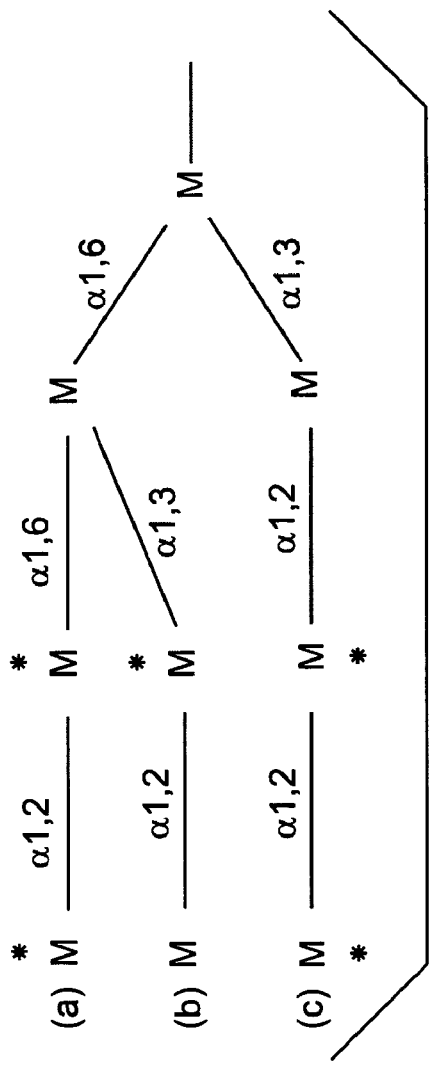
FIG. 13A is a schematic representation of the naturally occurring high mannose oligosaccharide (Man9) from which the synthetic bis-M6P glycan, shown in FIG. 13B, is derived.

Synthetic bis-M6P glycan was designed based on the in vivo process of M6P phosphorylation that occurs on naturally occurring high-mannose structure of lysosomal enzymes. (Kornfeld and Mellman, 5 ANNUAL REVIEW OF CELL BIOLOGY 483 (1989)). Synthetic bis-M6P oligomannose glycan was derived from the high mannose structure shown in FIG. 13A and was custom synthesized by BioMira (Edmonton, Alberta, Canada).

Figure 13B:
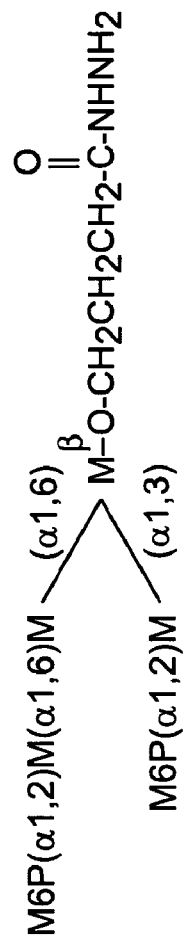

The middle antennary arm shown in (b) and one terminal mannose in (c) were removed, resulting in bis-M6P oligomannose, which was subsequently derivatized with a carbonyl reactive compound, butyryl hydrazide. The removal of the middle arm was believed to offer flexibility and improved pharmacokinetics by reducing competition against mannose receptors on macrophages and sinusoidal endothelial cells. This derivatized highly phosphorylated mannose oligosaccharide called bis-M6P-hydrazide, shown in FIG. 13B, was subsequently conjugated onto rhGAA.

B. Chemical Conjugation of Bis-M6P Hydrazide onto rhGAA

Recombinant human GAA (rhGAA) (Genzyme Corp.) was dialyzed twice against 4 liters of 0.1 M sodium acetate (pH 5.6) for 18 hours at 4° C. Approximately 10 mg/ml of dialyzed rhGAA was oxidized with 7.5 mM sodium meta-periodate for 30 minutes on ice. Excess sodium meta-periodate was removed by the addition of 50% glycerol and incubation on ice for 15 minutes. The oxidized rhGAA was then dialyzed against 4 liters of 0.1 M sodium acetate (pH 5.6). Five hundred milligrams of the oxidized rhGAA was conjugated to the bis-M6P-hydrazide by mixing and incubating at 37° C. for 2 hours. After conjugation, neoGAA samples were dialyzed three times against 4 liters of 25 mM sodium phosphate buffer (pH 6.75) containing 1% mannitol and 0.005% Tween-80 over 24 hours at 4° C. and then sterile filtered. The samples were aliquoted, snap-frozen on dry ice and stored at −80° C. until further analysis.

C. CI-MPR Column Fractionation and In Vitro Cell Uptake

Binding of neo-rhGAA and rhGAA to CI-MPR and in vitro uptake of rhGAA into L6 myoblast cells was evaluated essentially as described above. For uptake of GAAs into macrophages, NR8383 macrophage cells (ATCC, Manassas, Va.) were grown in T150 flasks. Prior to the uptake assay, cells were collected, washed once with Kaighan's media (Invitrogen) without serum and resuspended in uptake media (Kaighan's media+1.5% FBS+25 mM Hepes, pH6.8) at a concentration of $0.6-1\times10^6$ cells/ml. One ml of cells were aliquoted into microfuge tubes containing 25 nM of rhGAA or neo-rhGAA and to some of the tubes, either 2 mg/ml of yeast mannan was added to inhibit uptake mediated by mannose receptor, or 5 mM M6P to inhibit uptake mediated by CI-MPR. Uptake was continued for 2 hours at 37° C. and cells were harvested by centrifugation, washed twice with PBS containing 1 mM M6P and 1 mg/ml mannan, and then twice with PBS alone.

All cells were lysed in GAA assay buffer and assayed for GAA activity using 4-methylumbelliferyl-α-D-glucopyranoside as described above.

Figure 14A:
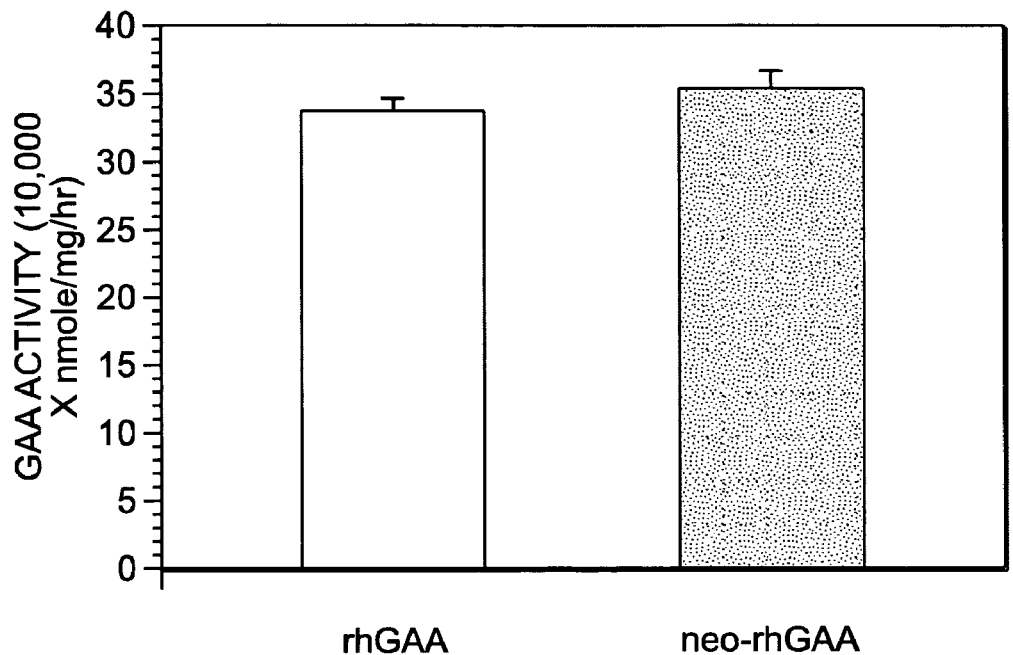
FIG. 14A depicts GM activity of the unmodified rhGAA and modified neo-rhGAA, conjugated with synthetic bis-M6P.
Figure 14B:
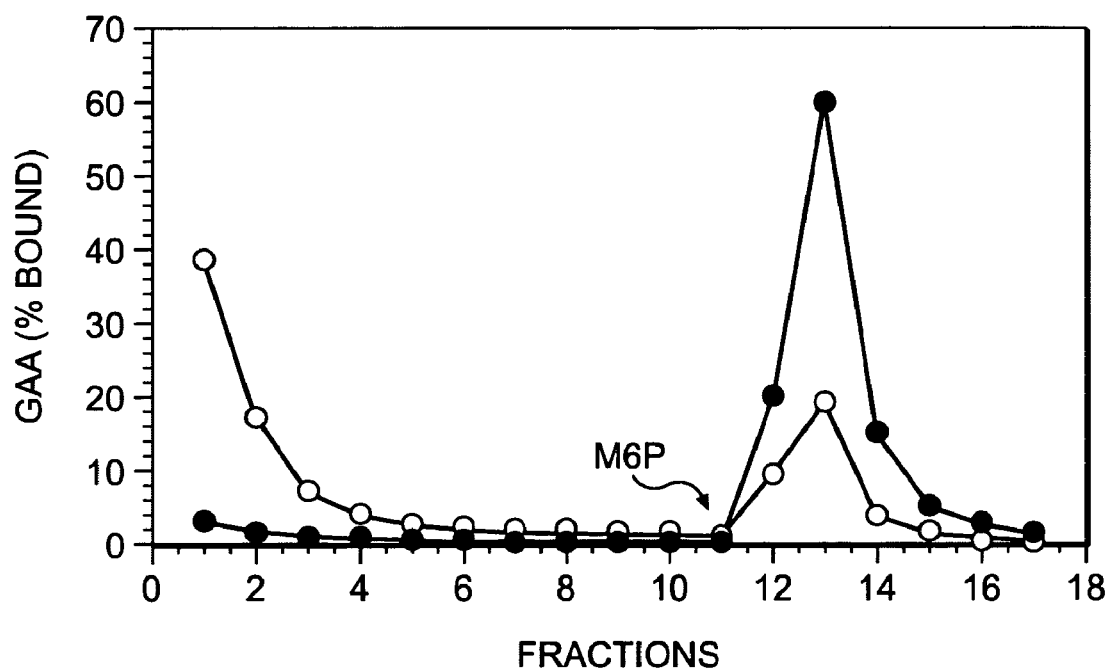
FIG. 14B depicts GM activity in fractions obtained following binding of rhGAA (open circles) and synthetic bis-M6P conjugated rhGAA (closed circles) to a CI-MPR column.

As depicted in FIG. 14A, direct conjugation of bis-M6P-hydrazide to periodate oxidized rhGAA did not affect its specific enzymatic activity. Furthermore, the neo-rhGAA thus generated had increased binding to the CI-MPR column, as depicted in FIG. 14B. In fact, more than 95% of neo-rhGAA now bound to the CI-MPR column compared to only about 30% of the unmodified rhGAA that bound to the column.

Consistent with the increased CI-MPR column binding, monosaccharide analysis of the neoGAA confirmed that the modified enzyme contained higher levels of phosphorylated oligomannose residues. The M6P content was increased from average of 0.9 mole M6P/mole of unmodified rhGAA to about 15 mole M6P/mole of neo-rhGAA, which translates to about 7 bis-M6P glycans conjugated onto the neo-rhGAA.

Figure 15A:
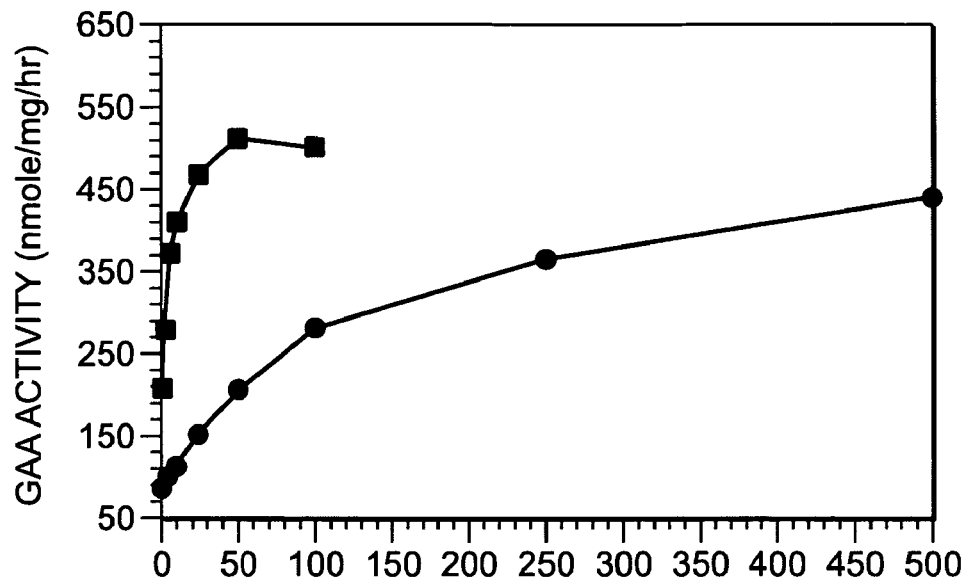
FIGS. 15A and 15B depict results of in vitro uptake assays in L6 myoblasts and macrophages, respectively.

Furthermore, consistent with a higher affinity for the CI-MPR, the neo-rhGAA also exhibited an improved uptake by L6 myoblasts. As shown in FIG. 15A, uptake of neo-rhGAA approached saturation at about 25 nM (closed squares) compared to approximately 500 nM for the unmodified rhGAA (closed circles). Uptake was blocked by the addition of excess M6P, confirming that the uptake of the enzyme by the L6 cells was primarily mediated via the CI-MPR. Based on the half maximal value of uptake, the dissociation constant (kd) of neo-rhGAA to CI-MPR was estimated to be around 2.5 nM, a value in agreement with the Kd of the natural bis-M6P oligosaccharides previously reported. (Tong et al., 264 J. BIOL. CHEM. 7962-7969 (1989)). In contrast, the Kd of the unmodified rhGAA to CI-MPR was about 100 nM, also close to the experimentally determined Kd for mono-M6P bearing oligosaccharides previously reported. (Distler et al., 266 J. BIOL. CHEM. 21687-21692 (1991)).

Figure 15B:
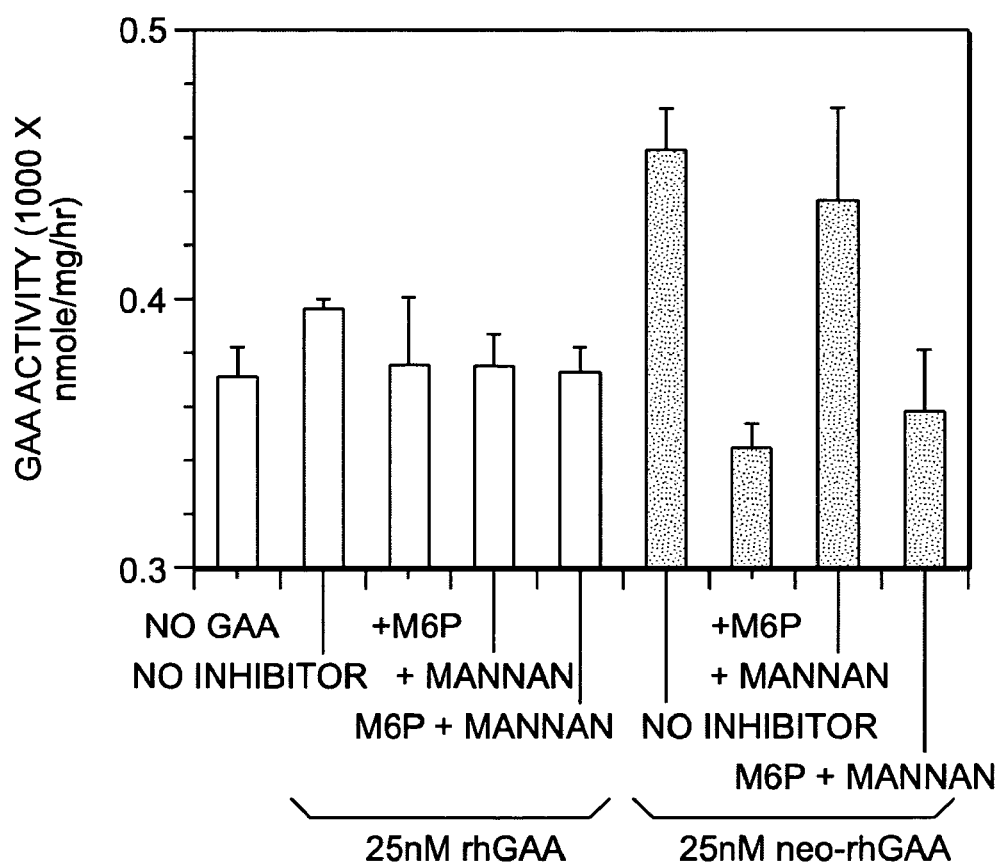

Mannose receptors on macrophage cells and sinusoidal endothelial cells are considered to be responsible for the clearance of glycoproteins in vivo by binding to mannose residues. In order to determine whether the addition of bis-M6P glycans on neo-rhGAA affects its uptake by mannose receptors, an in vitro cell uptake assay was performed with macrophages. As depicted in FIG. 15B, uptake of rhGAA was barely detectable after 2 hours even at 25 nM concentration. Furthermore, inclusion of inhibitors for CI-MPR and mannose receptor did not change the GAA activity in these cells. However, uptake of neo-rhGAA was readily detectable and was inhibited by M6P, but not by mannan, indicating that the increase in uptake into macrophages was mediated by M6P.

Example 10

Modifying rhGAA with bis-M6P Hydrazide Resulted in a Significant Improvement in Glycogen Clearance in Young Pompe Mice To determine whether the improved uptake and targeting properties of neo-rhGAA conjugated with synthetic glycan would result in a greater reduction in glycogen storage, young Pompe mice (5 months of age) were treated with either neo-rhGAA or unmodified rhGAA. Animal studies were conducted in accordance with the Guide for the Care and Use of Laboratory Animals (U.S. Department of Health and Human Services, NIH Publication No 86-23). Groups of Pompe mice (5-7 animals/group) were injected via the tail vein with vehicle and varying doses of either rhGAA or neo-rhGAA. Mice were administered four weekly doses and sacrificed one week after the last treatment. Various tissues including the heart, diaphragm and three skeletal muscles were retrieved and stored at −80° C. until further analysis. Statistical analysis was performed using one-way ANOVA followed by a Newman-Keuls test. A probability value of P<0.05 was considered statistically significant.

Glycogen content in the various muscles of the Pompe mice was assayed by measuring the difference in the amount of glucose released from a boiled tissue homogenate following digestion with or without *Aspergillus niger* amyloglucosidase, as described above. Glucose levels from the digested and undigested sample sets were then assayed using the Amplex Red glucose assay kit according to the manufacturer's instructions. Bovine liver glycogen was used as a standard. In some studies, glycogen content was measured using periodic acid Schiff (PAS) staining followed by computer-assisted histomorphometric analysis (Metamorph) as described above. All photography and MetaMorph analyses were performed in a blinded manner.

Figure 16:
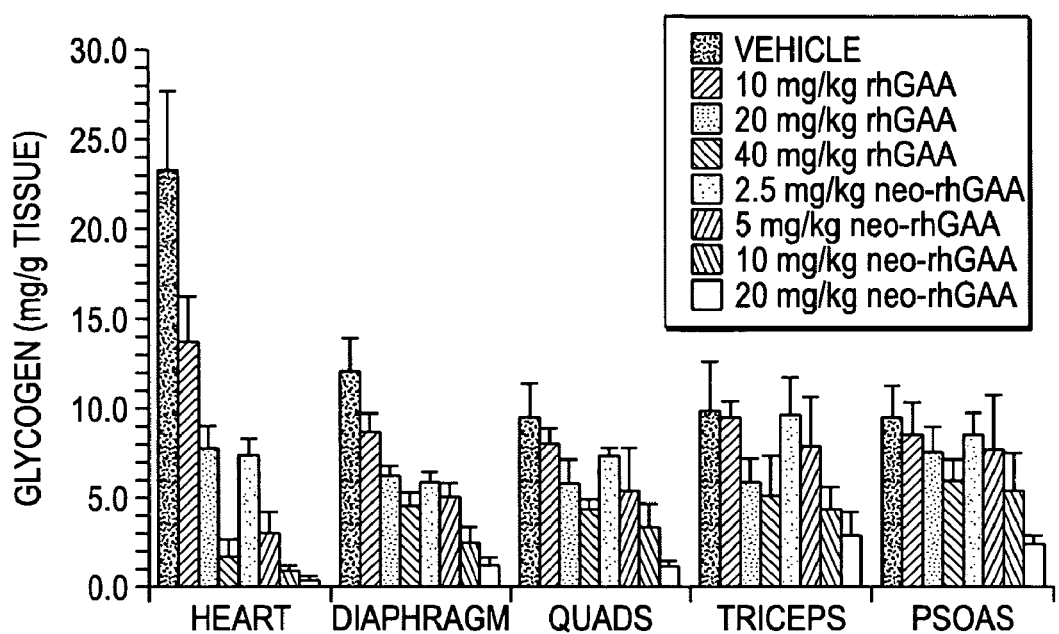
FIG. 16 is a bar graph showing glycogen levels, as assayed using the Amplex Red glucose assay, in representative tissues of young Pompe mice (4-5 months of age) following treatment with varying doses of vehicle alone, unmodified rhGAA or neo-rhGAA.

Treatment with either form of the enzyme resulted in a dose-dependent reduction in the glycogen levels in all the tissues examined, as depicted in FIG. 16. At equivalent doses, mice treated with neo-rhGAA uniformly displayed a greater extent of glycogen reduction in all the muscles analyzed, as shown in FIG. 16. In the heart and diaphragm, similar glycogen clearance was achieved with an approximately eight-fold reduced dose of neo-rhGAA relative to rhGAA. For example, 2.5 mg/kg and 5 mg/kg of neo-rhGAA achieved nearly the same glycogen reduction as 20 mg/kg and 40 mg/kg of rhGAA respectively. Significantly higher reduction in glycogen levels was also observed in skeletal muscles of animals that had been treated with the modified enzyme. Overall, the dose amount of modified rhGAA that was required to achieve a reduction in glycogen levels similar to that with rhGAA, was about four-fold less than the rhGAA in the quadriceps, triceps and psoas muscles examined.

Consistent with previous reports, the heart responded to GAA treatment better than the skeletal muscles which are generally more refractory to treatment, whether by rhGAA or neo-rhGAA. Four weekly doses of 10 mg/kg of neo-rhGAA completely cleared glycogen in the heart to normal levels, whereas 20 mg/kg of neo-rhGAA was required to clear glycogen in the diaphragm and quadriceps. However, for triceps and psoas, at 20 mg/kg dose, some glycogen remained in the muscles, as depicted in FIG. 16.

In an independent study with higher rhGAA and neo-rhGAA doses, it was observed that four weekly doses of 20 mg/kg of neo-rhGAA attained similar glycogen clearance as in case of 100 mg/kg rhGAA in the skeletal muscles, and 40 mg/kg of neo-rhGAA was required to clear glycogen in triceps and psoas muscles to near normal level (data not shown).

The reduction of glycogen observed by biochemical assay was confirmed by histomorphometric assessment of heart and quadriceps muscle samples obtained from the same study. By high resolution light microscopy, lysosomal glycogen appeared as discreet, purple beaded structures scattered throughout each myocyte. With enzyme treatment, these glycogen-containing structures become smaller and fewer in number. (data not shown). Administration of 20 mg/kg rhGAA resulted in clear reduction in the number of glycogen granules and percent tissue area occupied by glycogen in the heart when compared to vehicle treated samples; however, less discernible glycogen clearance was observed in quadriceps at this dose of rhGAA. In both cases, significant glycogen remained in tissues. In contrast, in both heart and quadriceps of Pompe animals treated with neo-rhGAA at this dose, near complete clearance of glycogen were attained. Occasionally, glycogen granules that appear to be cytoplasmic and resistant to treatment could be seen.

Example 11

Modifying rhGAA with Bis-M6P Hydrazide Resulted in a Significant Improvement in Glycogen Clearance in Old Pompe Mice The glycogen storage in old Pompe mice is more resistant to GAA treatment. This has been attributed, at least in part, to tissue damage in old mice that generally results in less efficient uptake of GAA by target muscle cells. To determine if neo-rhGAA would have similar beneficial effects in old Pompe animals, as in young mice, thirteen month old Pompe mice were used for evaluation. About 10 animals/group were treated with 40 mg/kg of either rhGAA or neo-rhGAA and the same tissues were harvested and assayed for glycogen content as for the younger mice.

Figure 17:
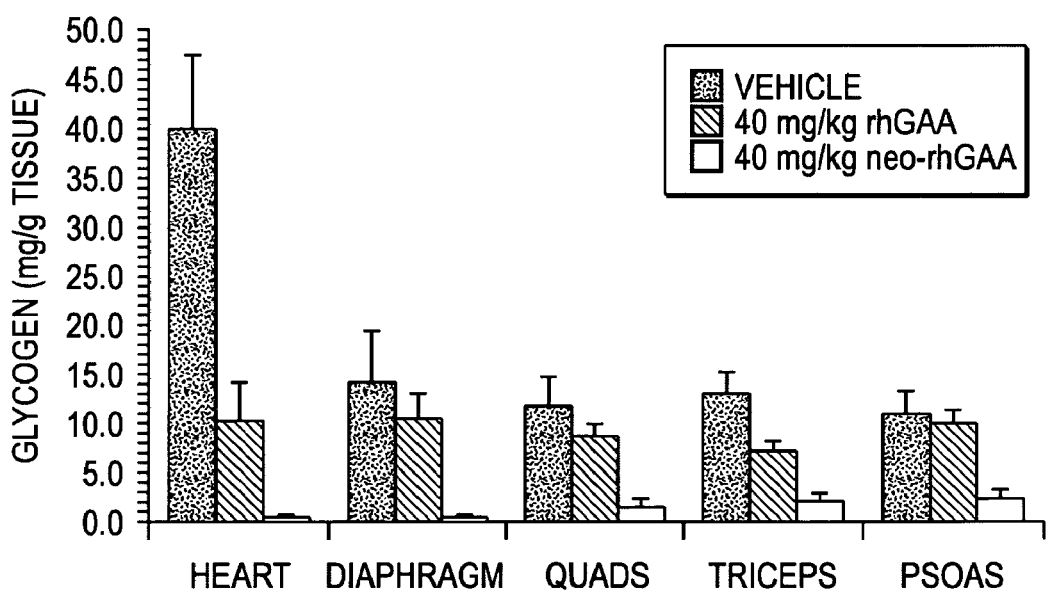
FIG. 17 is a bar graph showing glycogen levels, as assayed using the Amplex Red glucose assay, in representative tissues of old Pompe mice (13 months of age) following treatment with vehicle alone, 40 mg/kg of unmodified rhGAA or 40 mg/kg of neo-rhGAA.

As shown in FIG. 17, significantly less glycogen were cleared by 40 mg/kg of rhGAA in all the tissues examined, as compared to the young mice. From biochemical analysis of glycogen content, it was estimated that only about 80% of the glycogen were cleared in the heart, and only 10-40% of the glycogen was cleared from other tissues of old Pompe mice treated with rhGAA. However, despite being more refractory to rhGAA treatment, glycogen storages were completely cleared from the heart and diaphragm, >90% in quadriceps and >80% in triceps and psoas when these old animals were treated with 40 mg/kg of neo-rhGAA.

The increased glycogen clearance by neo-rhGAA over rhGAA in old Pompe mice were also confirmed by PAS staining and high resolution light microscopic analysis of representative tissues of the heart and quadriceps (data not shown). Again, as in case of young mice, glycogen granules appeared to be cytoplasmic and resistant to clearance were occasionally seen in few muscle cells.

All primary references cited herein are hereby incorporated by reference in their entirety, together with the references contained therein.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A modified lysosomal enzyme comprising a glycosylated lysosomal enzyme coupled to a biantennary oligosaccharide comprising:

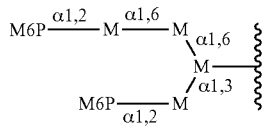

wherein M is mannose or a mannopyranosyl group and P is a phosphate group.

2. The modified lysosomal enzyme of claim 1, wherein the oligosaccharide is coupled to the glycosylated lysosomal enzyme through a carbon-nitrogen double bond.

3. The modified lysosomal enzyme of claim 2, wherein the carbon-nitrogen double bond is formed by reacting a carbonyl group on the glycosylated lysosomal enzyme with a carbonyl-reactive group on the oligosaccharide.

4. The modified lysosomal enzyme of claim 3, wherein the carbonyl-reactive group is chosen from a hydrazine, a hydrazide, an aminooxy, and a semicarbazide.

5. The modified lysosomal enzyme of claim 4, wherein the carbonyl-reactive group is aminooxy.

6. The modified lysosomal enzyme of claim 1, wherein the core mannose is attached to a linker through a β1 linkage.

7. The modified lysosomal enzyme of claim 1, wherein the lysosomal enzyme is acid alpha-glucosidase.

8. The modified lysosomal enzyme of claim 1, prepared by
 (a) derivatizing the biantennary oligosaccharide comprising a phosphorylated mannose with a compound containing a carbonyl-reactive group;
 (b) oxidizing at least one glycan on the glycosylated lysosomal enzyme to generate at least one carbonyl group; and
 (c) reacting the carbonyl-reactive group on the oligosaccharide with the carbonyl group on the glycosylated lysosomal enzyme, thereby coupling the oligosaccharide to the lysosomal enzyme.

9. The modified lysosomal enzyme of claim 8, wherein the carbonyl-reactive group is chosen from a hydrazine, a hydrazide, an aminooxy, and a semicarbazide.

10. The modified lysosomal enzyme of claim 9, wherein the carbonyl-reactive group is an aminooxy.

11. A composition comprising the modified lysosomal enzyme of claim 1.

12. A modified lysosomal enzyme comprising a glycosylated lysosomal enzyme coupled to a biantennary oligosaccharide comprising:

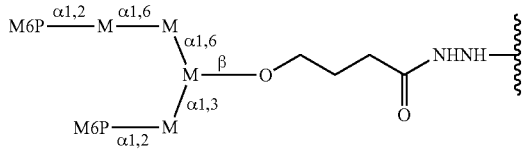

wherein M is mannose or a mannopyranosyl group and P is a phosphate group.

13. A composition comprising the modified lysosomal enzyme of claim 12.

14. The composition of claim 13, wherein the lysosomal enzyme is acid alpha-glucosidase.

15. A biantennary oligosaccharide comprising:

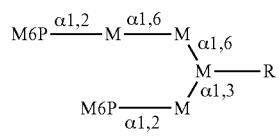

wherein R is a chemical group containing at least one carbonyl-reactive group.

16. The oligosaccharide of claim 15, wherein the at least one carbonyl-reactive group is chosen from a hydrazine, a hydrazide, an aminooxy, and a semicarbazide.

17. The oligosaccharide of claim 15, wherein R contains a hydrazine and an aminooxy.

18. A modified lysosomal enzyme comprising a glycosylated lysosomal enzyme coupled to the oligosaccharide of claim 17.

19. The modified lysosomal enzyme of claim 18, wherein the lysosomal enzyme is acid alpha-glucosidase.

20. A biantennary compound having the formula:

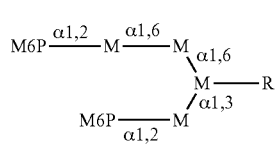

wherein R is a chemical group containing at least one carbonyl-reactive group.

21. A biantennary oligosaccharide comprising:

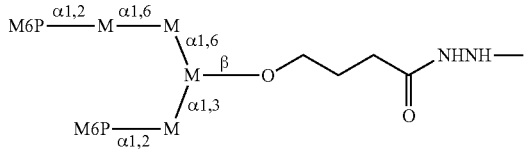

wherein M is mannose or a mannopyranosyl group and P is a phosphate group.

22. A biantennary compound having the formula:

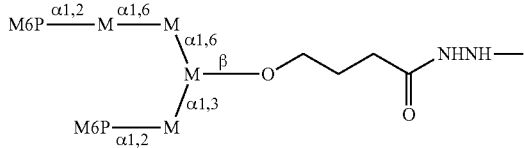

wherein M is mannose or a mannopyranosyl group and P is a phosphate group.

* * * * *

SEQUENCE LISTING

<160> NUMBER OF SEQ ID NOS: 2

<210> SEQ ID NO 1
<211> LENGTH: 2877
<212> TYPE: DNA
<213> ORGANISM: Artificial
<220> FEATURE:
<223> OTHER INFORMATION: recombinant human acid alpha glucosidase

<400> SEQUENCE: 1

```
ctcgagcaac catgggagtg aggcacccgc cctgctccca ccggctcctg gccgtctgcg      60
ccctcgtgtc cttggcaacc gctgcactcc tggggcacat cctactccat gatttcctgc     120
tggttccccg agagctgagt ggctcctccc cagtcctgga ggagactcac ccagctcacc     180
agcagggagc cagcagacca gggccccggg atgcccaggc acacccggcc cgtcccagag     240
cagtgcccac acagtgcgac gtccccccca acagccgctt cgattgcgcc cctgacaagg     300
ccatcacccc ggaacagtgc gaggcccgcg gctgctgcta catccctgca aagcaggggc     360
tgcagggagc ccagatgggg cagccctggt gcttcttccc acccagctac cccagctaca     420
agctggagaa cctgagctcc tctgaaatgg gctacacggc cacctgacc cgtaccaccc     480 ccaccttctt ccccaaggac atcctgaccc tgcggctgga cgtgatgatg gagactgaga     540
accgcctcca cttcacgatc aaagatccag ctaacaggcg ctacgaggtg cccttggaga     600
ccccgcgtgt ccacagccgg gcaccgtccc cactctacag cgtggagttc tctgaggagc     660
```

```
ccttcggggt gatcgtgcac cggcagctgg acggccgcgt gctgctgaac acgacggtgg    720
cgccctgtt ctttgcggac cagttccttc agctgtccac ctcgctgccc tcgcagtata    780
tcacaggcct cgccgagcac ctcagtcccc tgatgctcag caccagctgg accaggatca    840
ccctgtggaa ccgggacctt gcgcccacgc ccggtgcgaa cctctacggg tctcacccct    900
tctacctggc gctggaggac ggcgggtcgg cacacgggt gttcctgcta aacagcaatg    960
ccatggatgt ggtcctgcag ccgagccctg cccttagctg gaggtcgaca ggtgggatcc   1020
tggatgtcta catcttcctg ggcccagagc ccaagagcgt ggtgcagcag tacctggacg   1080
ttgtgggata cccgttcatg ccgccatact ggggcctggg cttccacctg tgccgctggg   1140
gctactcctc caccgctatc acccgccagg tggtggagaa catgaccagg gcccacttcc   1200
ccctggacgt ccaatggaac gacctggact acatggactc ccggagggac ttcacgttca   1260
acaaggatgg cttccgggac ttcccggcca tggtgcagga gctgcaccag ggcggccggc   1320
gctacatgat gatcgtggat cctgccatca gcagctcggg ccctgccggg agctacaggc   1380
cctacgacga gggtctgcgg agggggggttt tcatcaccaa cgagaccggc cagccgctga   1440
ttgggaaggt atgccccggg tccactgcct tccccgactt caccaacccc acagccctgg   1500
cctggtggga ggacatggtg gctgagttcc atgaccaggt gcccttcgac ggcatgtgga   1560
ttgacatgaa cgagccttcc aacttcatca ggggctctga ggacggctgc cccaacaatg   1620
agctggagaa cccacccta cgtgcctggg tggttggggg gaccctccag gcggccacca   1680
tctgtgcctc cagccaccag tttctctcca cacactacaa cctgcacaac ctctacggcc   1740
tgaccgaagc catcgcctcc cacagggcgc tggtgaaggc tcgggggaca cgcccatttg   1800
tgatctcccg ctcgacccttt gctggccacg gccgatacgc cggccactgg acggggacg   1860
tgtggagctc ctgggagcag ctcgcctcct ccgtgccaga aatcctgcag tttaacctgc   1920
tgggggtgcc tctggtcggg gccgacgtct gcggcttcct gggcaacacc tcagaggagc   1980
tgtgtgtgcg ctggacccag ctgggggcct tctacccctt catgcggaac acaacagcc   2040
tgctcagtct gccccaggag ccgtacagct cagcgagcc ggcccagcag gccatgagga   2100
aggccctcac cctgcgctac gcactcctcc cccacctcta cacgctgttc caccaggccc   2160
acgtcgcggg ggagaccgtg gcccggcccc tcttcctgga gttccccaag gactctagca   2220
cctggactgt ggaccaccag ctcctgtggg gggaggccct gctcatcacc ccagtgctcc   2280
aggccgggaa ggccgaagtg actggctact tccccttggg cacatggtac gacctgcaga   2340
cggtgccaat agaggccctt ggcagcctcc acccccacc tgcagctccc cgtgagccag   2400
ccatccacag cgaggggcag tgggtgacgc tgccggcccc cctggacacc atcaacgtcc   2460
acctccgggc tgggtacatc atccccctgc agggccctgg cctcacaacc acagagtccc   2520
gccagcagcc catggccctg ctgtgggccc tgaccaaggg tggagaggcc cgaggggagc   2580
tgttctggga cgatggagag agcctggaag tgctggagcg aggggcctac acacaggtca   2640
tcttcctggc caggaataac acgatcgtga atgagctggt acgtgtgacc agtgagggag   2700
ctggcctgca gctgcagaag gtgactgtcc tgggcgtggc cacggcgccc cagcaggtcc   2760
tctccaacgg tgtccctgtc tccaacttca cctacagccc cgacaccaag gtcctggaca   2820
tctgtgtctc gctgttgatg ggagagcagt ttctcgtcag ctggtgttaa actcgag     2877
```

<210> SEQ ID NO 2
<211> LENGTH: 952
<212> TYPE: PRT
<213> ORGANISM: Artificial

```
<220> FEATURE:
<223> OTHER INFORMATION: recombinant human acid alpha glucosidase
<220> FEATURE:
<221> NAME/KEY: recombinant human acid alpha glucosidase
<222> LOCATION: (1)..(952)
<223> OTHER INFORMATION:

<400> SEQUENCE: 2
```

| | | | | | | | | | | | | | | |
|---|---|---|---|---|---|---|---|---|---|---|---|---|---|---|
| Met | Gly | Val | Arg | His | Pro | Pro | Cys | Ser | His | Arg | Leu | Leu | Ala | Val | Cys |
| 1 | | | | 5 | | | | | 10 | | | | | 15 |
| Ala | Leu | Val | Ser | Leu | Ala | Thr | Ala | Ala | Leu | Leu | Gly | His | Ile | Leu | Leu |
| | | | 20 | | | | | 25 | | | | | 30 | | |
| His | Asp | Phe | Leu | Leu | Val | Pro | Arg | Glu | Leu | Ser | Gly | Ser | Ser | Pro | Val |
| | | 35 | | | | | 40 | | | | | 45 | | | |
| Leu | Glu | Glu | Thr | His | Pro | Ala | His | Gln | Gln | Gly | Ala | Ser | Arg | Pro | Gly |
| | 50 | | | | | 55 | | | | | 60 | | | | |
| Pro | Arg | Asp | Ala | Gln | Ala | His | Pro | Gly | Arg | Pro | Arg | Ala | Val | Pro | Thr |
| 65 | | | | | 70 | | | | | 75 | | | | | 80 |
| Gln | Cys | Asp | Val | Pro | Pro | Asn | Ser | Arg | Phe | Asp | Cys | Ala | Pro | Asp | Lys |
| | | | | 85 | | | | | 90 | | | | | 95 | |
| Ala | Ile | Thr | Gln | Glu | Gln | Cys | Glu | Ala | Arg | Gly | Cys | Cys | Tyr | Ile | Pro |
| | | | 100 | | | | | 105 | | | | | 110 | | |
| Ala | Lys | Gln | Gly | Leu | Gln | Gly | Ala | Gln | Met | Gly | Gln | Pro | Trp | Cys | Phe |
| | | 115 | | | | | 120 | | | | | 125 | | | |
| Phe | Pro | Pro | Ser | Tyr | Pro | Ser | Tyr | Lys | Leu | Glu | Asn | Leu | Ser | Ser | Ser |
| | 130 | | | | | 135 | | | | | 140 | | | | |
| Glu | Met | Gly | Tyr | Thr | Ala | Thr | Leu | Thr | Arg | Thr | Thr | Pro | Thr | Phe | Phe |
| 145 | | | | | 150 | | | | | 155 | | | | | 160 |
| Pro | Lys | Asp | Ile | Leu | Thr | Leu | Arg | Leu | Asp | Val | Met | Met | Glu | Thr | Glu |
| | | | | 165 | | | | | 170 | | | | | 175 | |
| Asn | Arg | Leu | His | Phe | Thr | Ile | Lys | Asp | Pro | Ala | Asn | Arg | Arg | Tyr | Glu |
| | | | 180 | | | | | 185 | | | | | 190 | | |
| Val | Pro | Leu | Glu | Thr | Pro | Arg | Val | His | Ser | Arg | Ala | Pro | Ser | Pro | Leu |
| | | 195 | | | | | 200 | | | | | 205 | | | |
| Tyr | Ser | Val | Glu | Phe | Ser | Glu | Glu | Pro | Phe | Gly | Val | Ile | Val | His | Arg |
| | 210 | | | | | 215 | | | | | 220 | | | | |
| Gln | Leu | Asp | Gly | Arg | Val | Leu | Leu | Asn | Thr | Thr | Val | Ala | Pro | Leu | Phe |
| 225 | | | | | 230 | | | | | 235 | | | | | 240 |
| Phe | Ala | Asp | Gln | Phe | Leu | Gln | Leu | Ser | Thr | Ser | Leu | Pro | Ser | Gln | Tyr |
| | | | | 245 | | | | | 250 | | | | | 255 | |
| Ile | Thr | Gly | Leu | Ala | Glu | His | Leu | Ser | Pro | Leu | Met | Leu | Ser | Thr | Ser |
| | | | 260 | | | | | 265 | | | | | 270 | | |
| Trp | Thr | Arg | Ile | Thr | Leu | Trp | Asn | Arg | Asp | Leu | Ala | Pro | Thr | Pro | Gly |
| | | 275 | | | | | 280 | | | | | 285 | | | |
| Ala | Asn | Leu | Tyr | Gly | Ser | His | Pro | Phe | Tyr | Leu | Ala | Leu | Glu | Asp | Gly |
| | 290 | | | | | 295 | | | | | 300 | | | | |
| Gly | Ser | Ala | His | Gly | Val | Phe | Leu | Leu | Asn | Ser | Asn | Ala | Met | Asp | Val |
| 305 | | | | | 310 | | | | | 315 | | | | | 320 |
| Val | Leu | Gln | Pro | Ser | Pro | Ala | Leu | Ser | Trp | Arg | Ser | Thr | Gly | Gly | Ile |
| | | | | 325 | | | | | 330 | | | | | 335 | |
| Leu | Asp | Val | Tyr | Ile | Phe | Leu | Gly | Pro | Glu | Pro | Lys | Ser | Val | Val | Gln |
| | | | 340 | | | | | 345 | | | | | 350 | | |
| Gln | Tyr | Leu | Asp | Val | Val | Gly | Tyr | Pro | Phe | Met | Pro | Pro | Tyr | Trp | Gly |
| | | 355 | | | | | 360 | | | | | 365 | | | |
| Leu | Gly | Phe | His | Leu | Cys | Arg | Trp | Gly | Tyr | Ser | Ser | Thr | Ala | Ile | Thr |
| | 370 | | | | | 375 | | | | | 380 | | | | |

```
Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
            405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
            435                 440                 445

Ser Gly Pro Ala Gly Ser Tyr Arg Pro Tyr Asp Glu Gly Leu Arg Arg
            450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
            485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
            515                 520                 525

Ser Glu Asp Gly Cys Pro Asn Asn Glu Leu Glu Asn Pro Pro Tyr Val
            530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
            565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
            595                 600                 605

Tyr Ala Gly His Trp Thr Gly Asp Val Trp Ser Ser Trp Glu Gln Leu
            610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
            645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
            675                 680                 685

Glu Pro Ala Gln Gln Ala Met Arg Lys Ala Leu Thr Leu Arg Tyr Ala
            690                 695                 700

Leu Leu Pro His Leu Tyr Thr Leu Phe His Gln Ala His Val Ala Gly
705                 710                 715                 720

Glu Thr Val Ala Arg Pro Leu Phe Leu Glu Phe Pro Lys Asp Ser Ser
            725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
            755                 760                 765

Leu Gly Thr Trp Tyr Asp Leu Gln Thr Val Pro Ile Glu Ala Leu Gly
            770                 775                 780

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
```

|   |   |   |   |   |   |   |   |   |   |   |   |
|---|---|---|---|---|---|---|---|---|---|---|---|
|   |   |   | 805 |   |   |   | 810 |   |   | 815 |   |
| His | Leu | Arg | Ala | Gly | Tyr | Ile | Ile | Pro | Leu | Gln | Gly | Pro | Gly | Leu | Thr |
|   |   |   | 820 |   |   |   | 825 |   |   | 830 |   |
| Thr | Thr | Glu | Ser | Arg | Gln | Gln | Pro | Met | Ala | Leu | Ala | Val | Ala | Leu | Thr |
|   |   |   | 835 |   |   |   | 840 |   |   | 845 |   |
| Lys | Gly | Gly | Glu | Ala | Arg | Gly | Glu | Leu | Phe | Trp | Asp | Asp | Gly | Glu | Ser |
|   |   |   | 850 |   |   |   | 855 |   |   | 860 |   |
| Leu | Glu | Val | Leu | Glu | Arg | Gly | Ala | Tyr | Thr | Gln | Val | Ile | Phe | Leu | Ala |
| 865 |   |   |   |   | 870 |   |   |   | 875 |   |   |   |   |   | 880 |
| Arg | Asn | Asn | Thr | Ile | Val | Asn | Glu | Leu | Val | Arg | Val | Thr | Ser | Glu | Gly |
|   |   |   |   |   | 885 |   |   |   | 890 |   |   |   | 895 |   |   |
| Ala | Gly | Leu | Gln | Leu | Gln | Lys | Val | Thr | Val | Leu | Gly | Val | Ala | Thr | Ala |
|   |   |   | 900 |   |   |   | 905 |   |   | 910 |   |
| Pro | Gln | Gln | Val | Leu | Ser | Asn | Gly | Val | Pro | Val | Ser | Asn | Phe | Thr | Tyr |
|   |   |   | 915 |   |   |   | 920 |   |   | 925 |   |
| Ser | Pro | Asp | Thr | Lys | Val | Leu | Asp | Ile | Cys | Val | Ser | Leu | Leu | Met | Gly |
|   |   |   | 930 |   |   |   | 935 |   |   | 940 |   |
| Glu | Gln | Phe | Leu | Val | Ser | Trp | Cys |
| 945 |   |   |   |   | 950 |   |   |